United States Patent
Berger

(10) Patent No.: US 6,330,883 B1
(45) Date of Patent: Dec. 18, 2001

(54) HEAT AND MOISTURE EXCHANGER COMPRISING HYDROPHILIC NYLON AND METHODS OF USING SAME

(75) Inventor: Richard M. Berger, Midlothian, VA (US)

(73) Assignee: Filtrona Richmond, Inc., Colonial Heights, VA (US)

( * ) Notice: Subject to any disclaimer, the term of this patent is extended or adjusted under 35 U.S.C. 154(b) by 0 days.

(21) Appl. No.: 09/251,491

(22) Filed: Feb. 17, 1999

(51) Int. Cl.[7] .................................................. A62B 18/08
(52) U.S. Cl. ........................ 128/201.13; 128/201.25; 128/203.26; 128/204.15; 128/204.16; 128/204.17; 128/205.12
(58) Field of Search ................ 128/201.13, 201.25, 128/203.26, 204.15, 204.16, 204.17, 205.12, 205.27

(56) References Cited

U.S. PATENT DOCUMENTS

| | | |
|---|---|---|
| 2,411,660 | 11/1946 | Manning . |
| 3,881,482 * | 5/1975 | Lindholm ........................ 128/207.15 |
| 4,048,993 * | 9/1977 | Dobritz ............................ 128/204.23 |
| 4,438,167 | 3/1984 | Schwarz . |
| 4,449,992 * | 5/1984 | Yamada et al. ........................ 55/158 |
| 4,771,770 * | 9/1988 | Artemenko et al. ............ 128/201.13 |
| 5,162,074 | 11/1992 | Hills . |
| 5,349,946 | 9/1994 | McComb . |
| 5,482,031 | 1/1996 | Lambert . |
| 5,509,430 | 4/1996 | Berger . |
| 5,577,494 | 11/1996 | Kuypers et al. . |
| 5,586,997 * | 12/1996 | Pall et al. ................................ 55/361 |
| 5,607,766 * | 3/1997 | Berger ................................. 428/373 |
| 5,620,641 | 4/1997 | Berger . |
| 5,633,082 * | 5/1997 | Berger ................................. 428/365 |
| 5,829,428 | 11/1998 | Walters et al. . |
| 6,103,181 * | 8/2000 | Berger ................................. 264/555 |

OTHER PUBLICATIONS

"HALAR® ECTFE", Ausimont USA, Inc., 7/96.
"Bicomponent Fibers: A Personal Perspective", IFJ, Jun. 1998, pp. 26–42.

(List continued on next page.)

*Primary Examiner*—Aaron J. Lewis
*Assistant Examiner*—Joseph F. Weiss, Jr.
(74) *Attorney, Agent, or Firm*—Jacobson Holman, PLLC

(57) ABSTRACT

A heat and moisture exchanger including a gas-permeable element, preferably a fibrous media, adapted to be warmed and to trap moisture from a patient's breath during exhalation and to be cooled and to release the trapped moisture for return to the patient during inspiration to effectively conserve the humidity and body heat of the patient's respiratory tract, wherein the media comprises a hydrophilic nylon polymer. The gas-permeable element can be formed entirely of monocomponent fibers of the hydrophilic nylon polymer or, preferably, fibers comprising at least a sheath of the hydrophilic nylon polymer can be bonded at their points of contact by a bonding agent, such as a polyester. Bicomponent fibers comprising a sheath of the hydrophilic nylon polymer can be bonded by other bicomponent fibers comprising a sheath of the bonding agent, with all of the bicomponent fibers comprising a core of a thermoplastic polymer, such as polypropylene, to minimize the cost and increase the strength of the heat and moisture exchanger element.

39 Claims, 20 Drawing Sheets

OTHER PUBLICATIONS

"Filters and Heat & Moisture Exchangers", SIMS, Inc., 1997, pp. 1–8.

"Viral Removal By Pall Breating Circuit Filters", Pall Technical Report, 1988, 4 pages.

"Pall Bicomedical Filters for OEM Applications", Pall Corporation, 1987, 2 pages.

"Pall Home Respiratory Therapy Filters", Pall Biomedical Products Corp., 2 pages.

"With Every Breath . . . Pall Breathing Circuit Filters", Pall Corporation, 1988, 2 pages.

"A Comparison of Five Heat and Moisture Exchangers", Shelly et al, Anaesthesia, 1986, vol. 41, pp. 527–532.

"Endotracheal Tube Occlusion Associated With the Use of Heat and Moisture . . . ", Cohen, M.D., et al, Critical Care Med., 1988, pp. 277–279.

"Health Devices", Emergency Care Research Inst., 1983, vol. 12, No. 7, pp. 155–167.

"The Pall Corporation Heat and Moisture Exchanger", Pall Biomed. Products Corp., 1985, pp. 1–8.

"Hydrophillic Nylon for the Nonwovens Industry", Susan Kerr, pp. 1–7.

"New Concepts in Melt–Blown Design Applied to . . . ", Eckhard Schwarz Biax–Fiberfilm Corp., Mar. 1987, pp. 206–220.

* cited by examiner

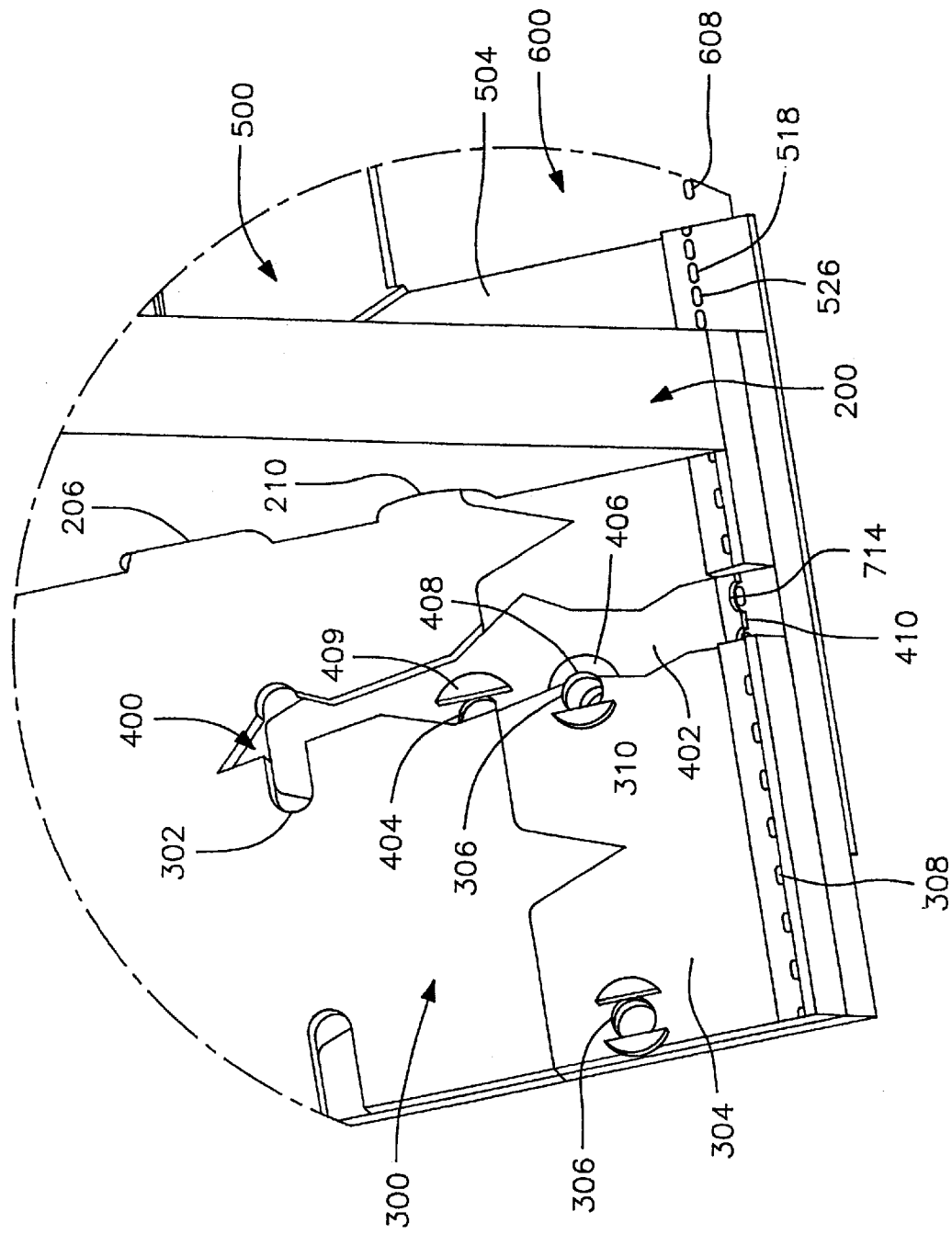

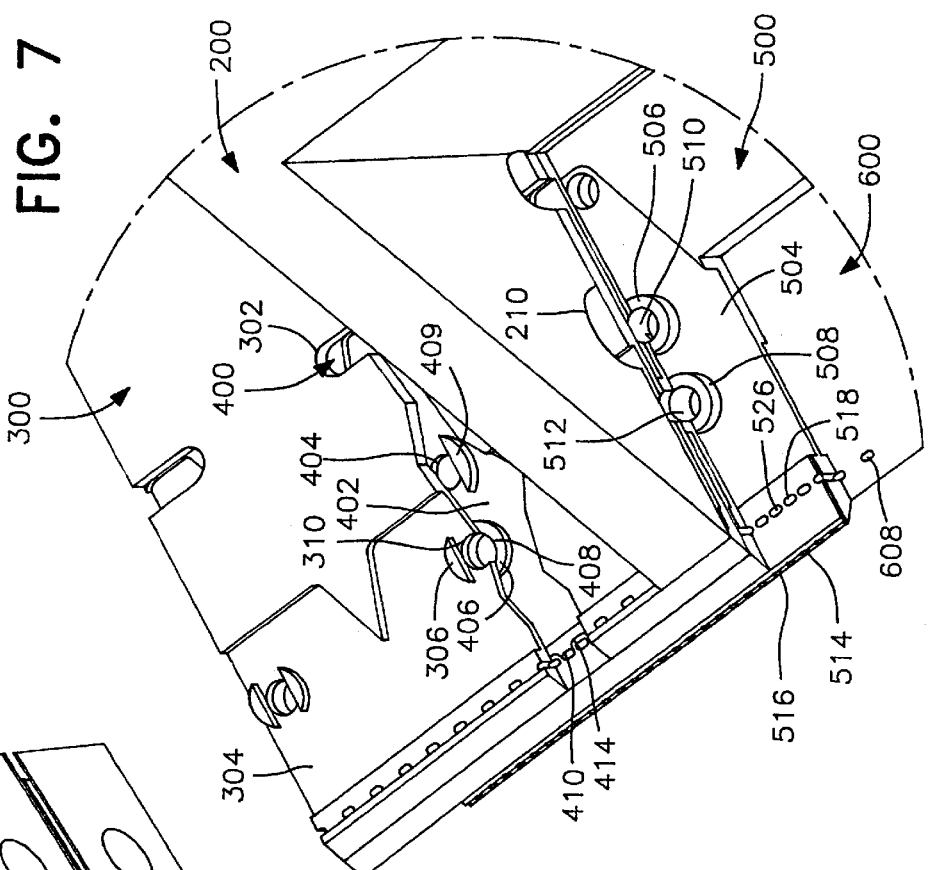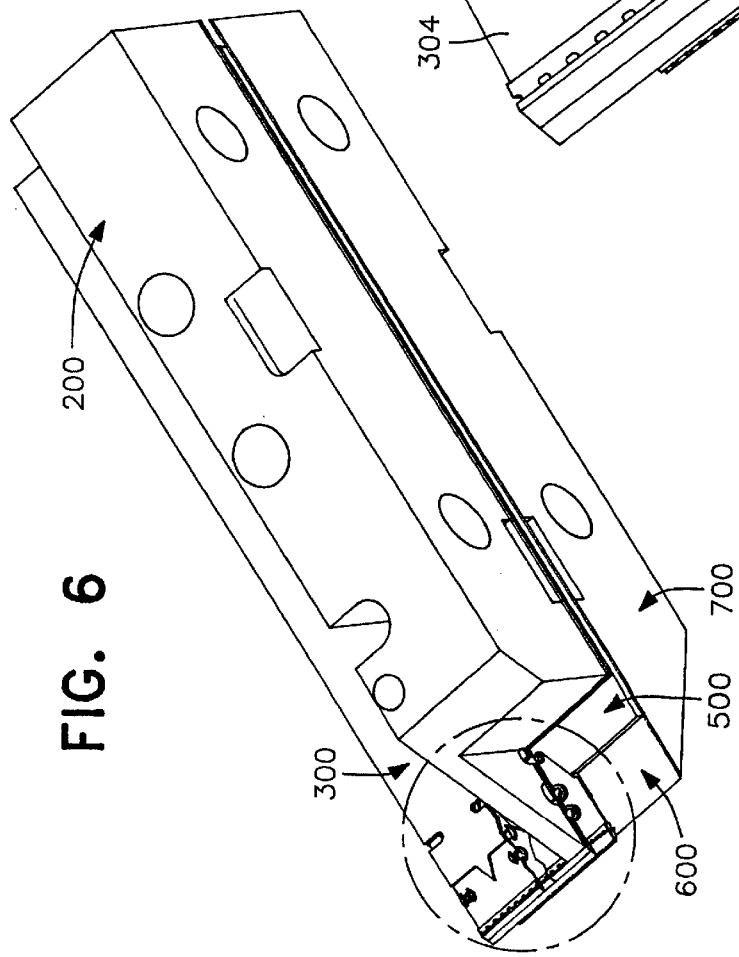

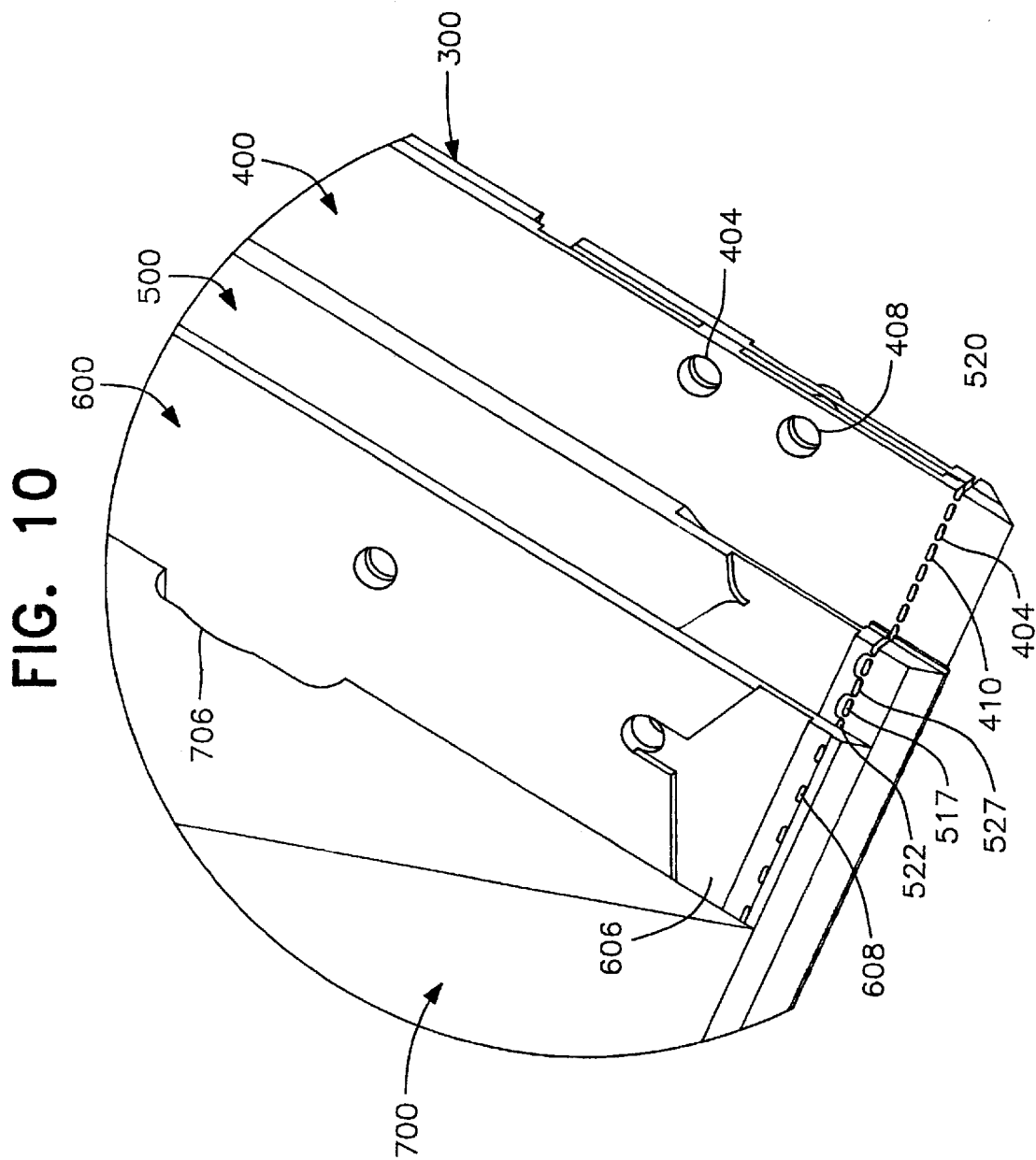

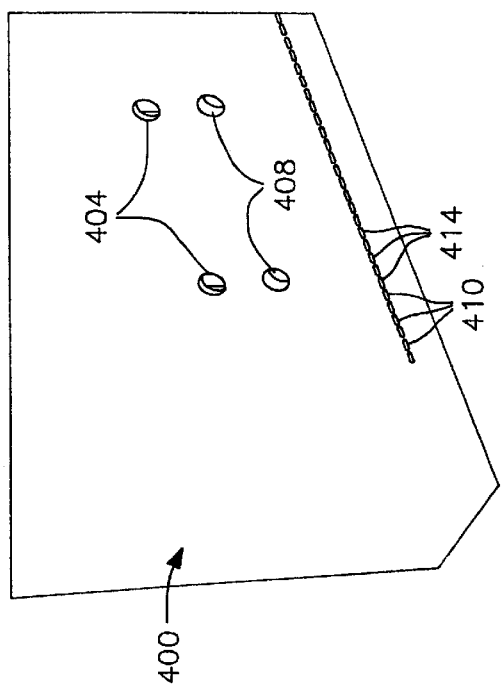
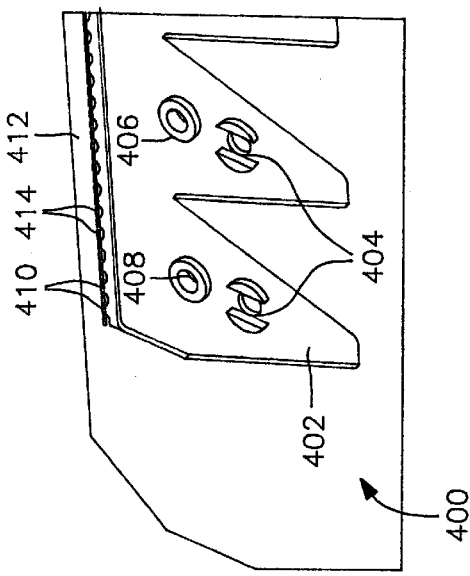
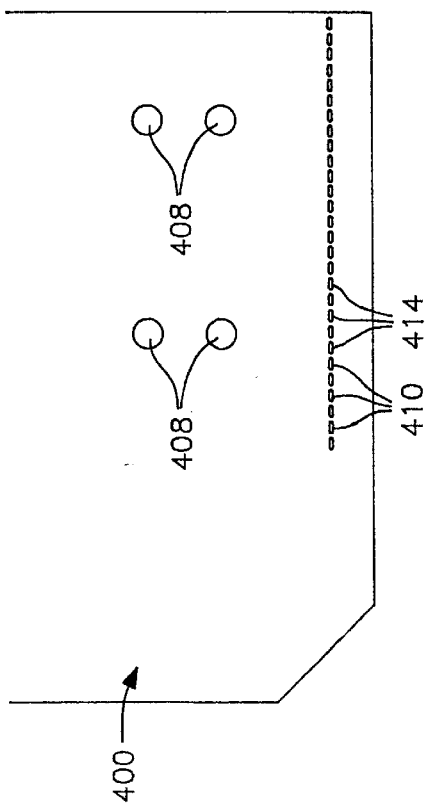
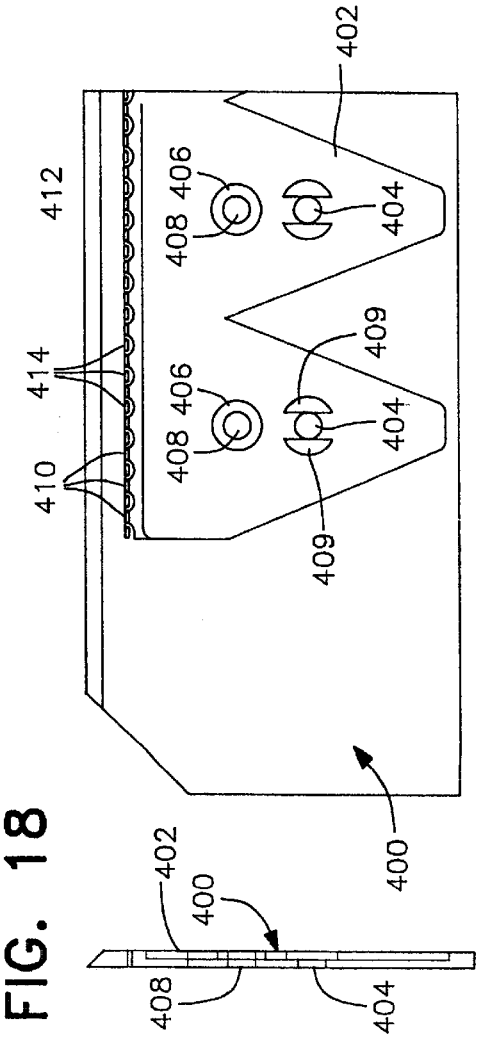

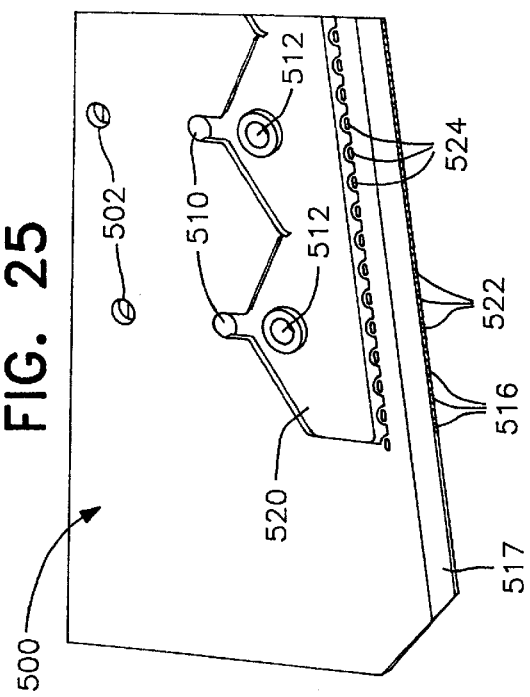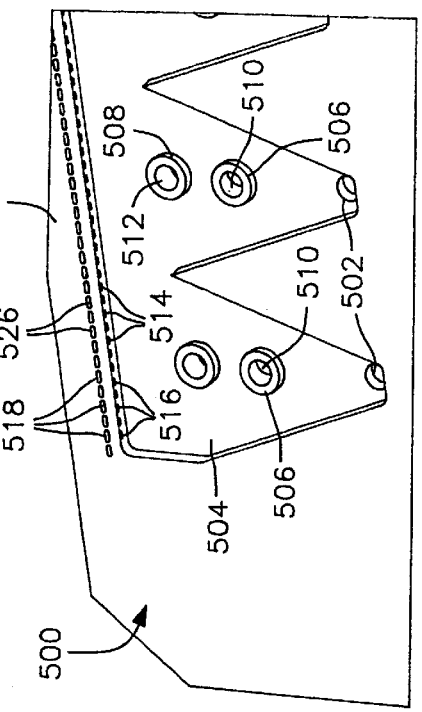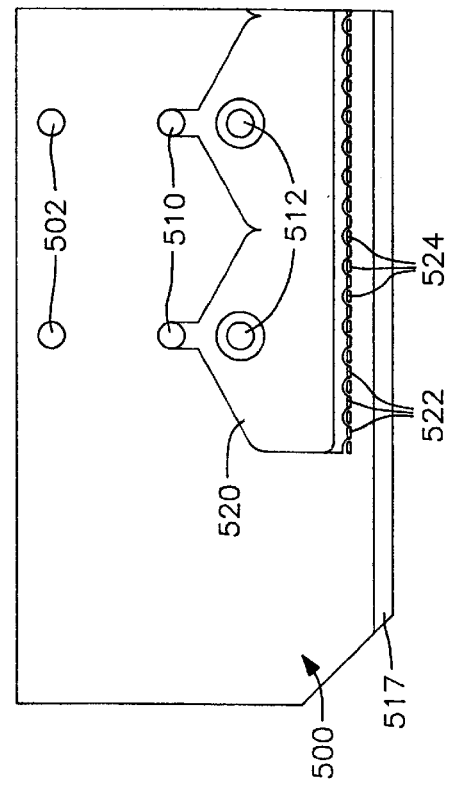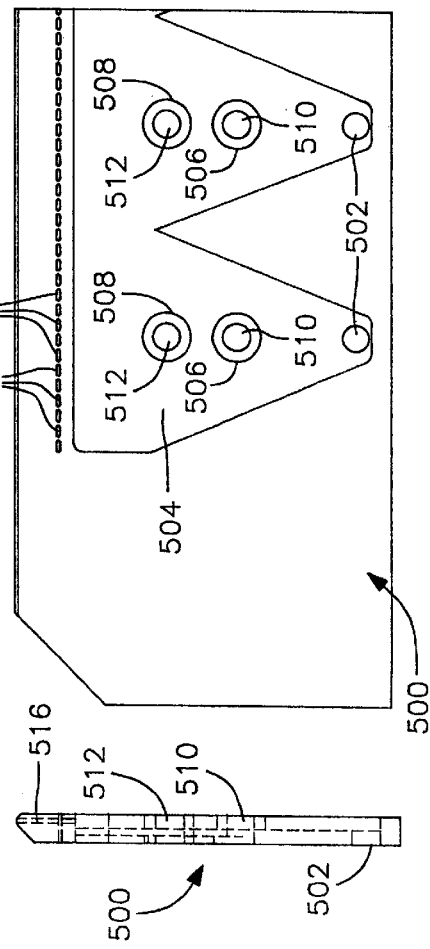

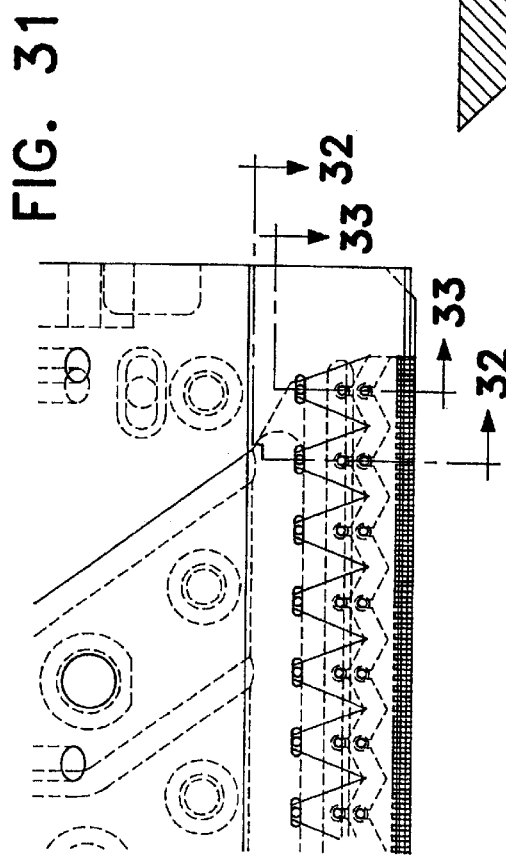
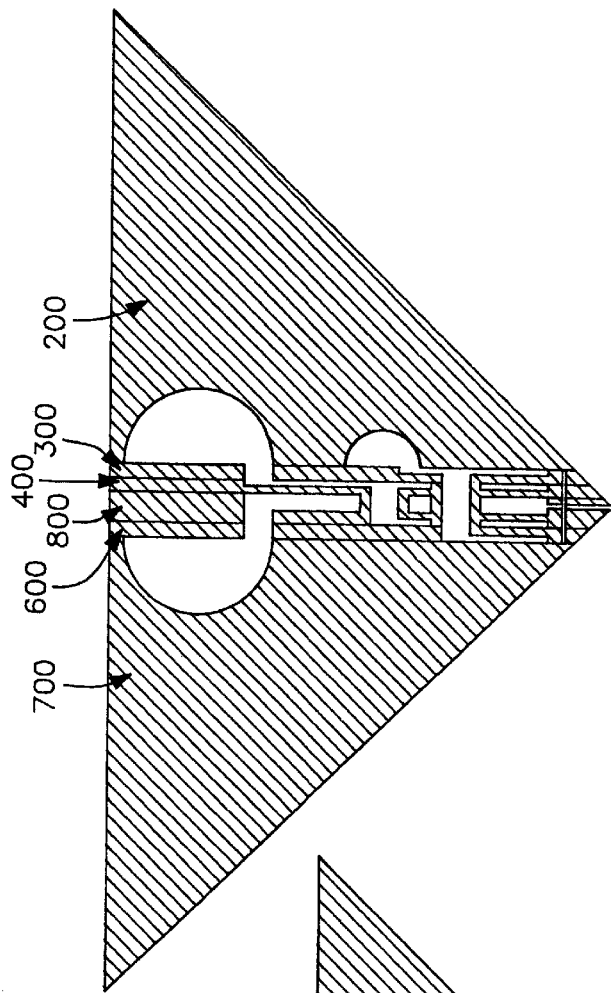
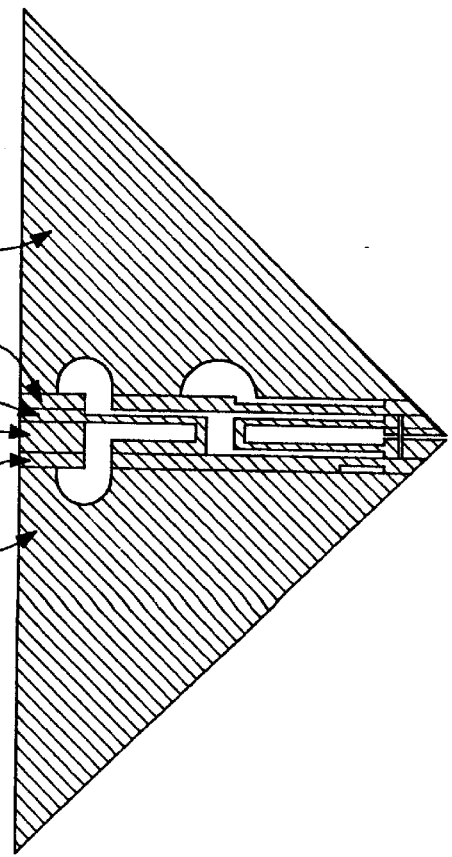

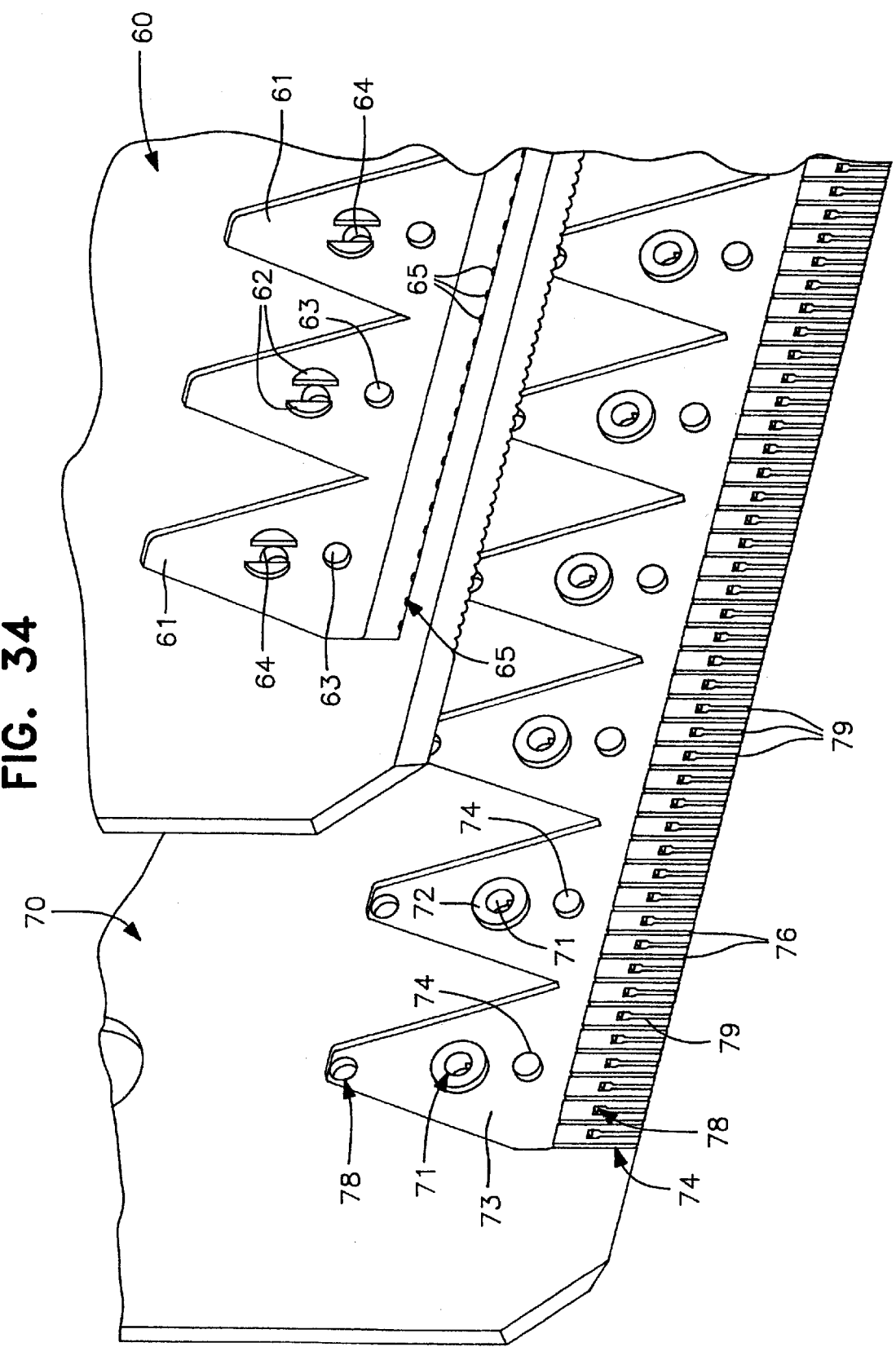

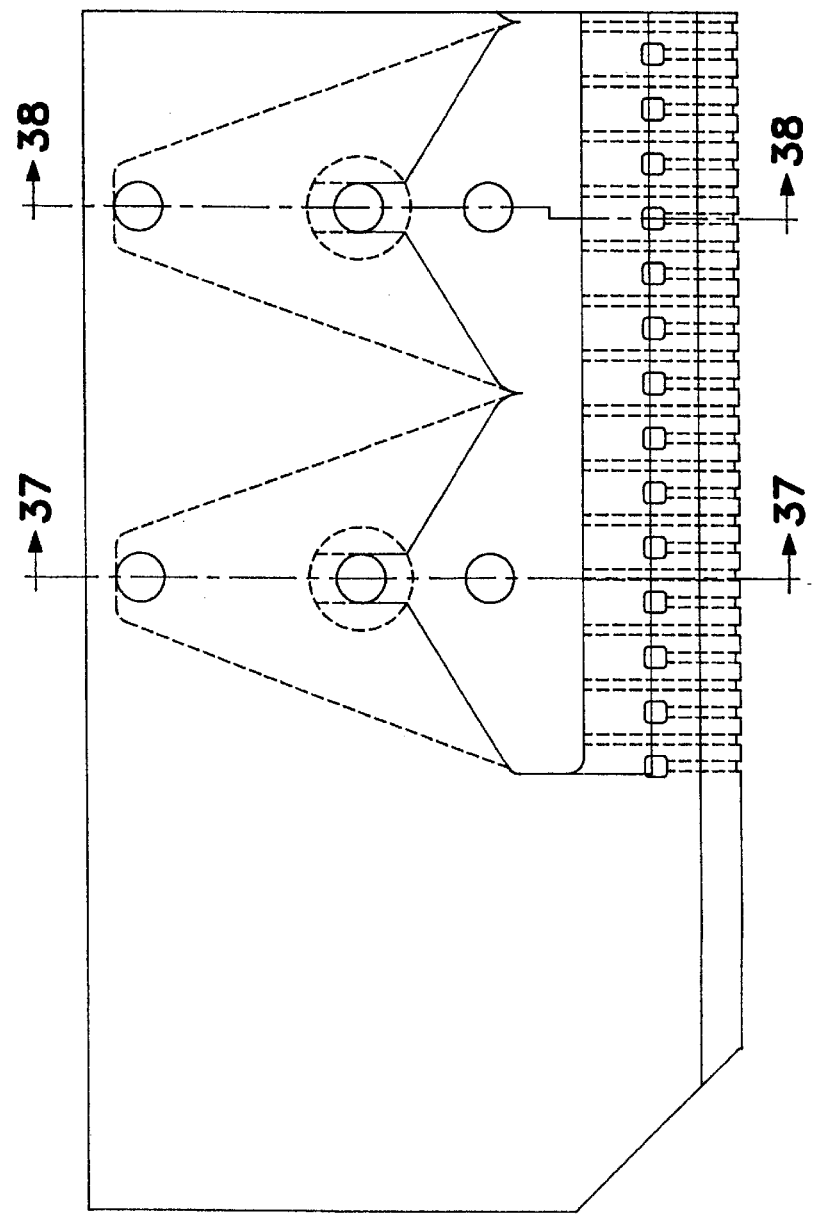

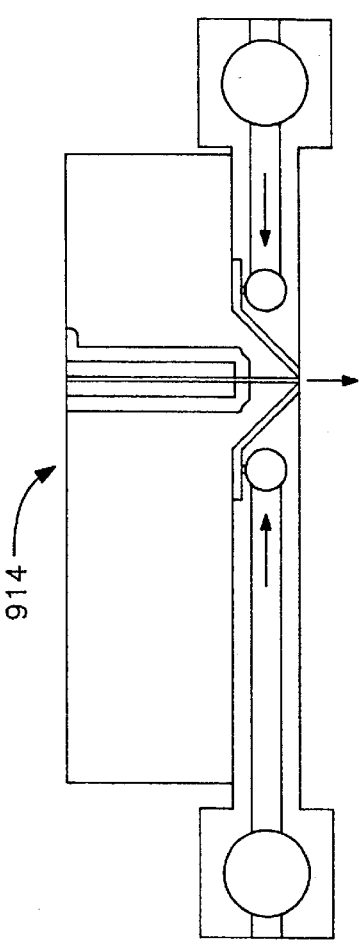
FIG. 46
FIG. 45
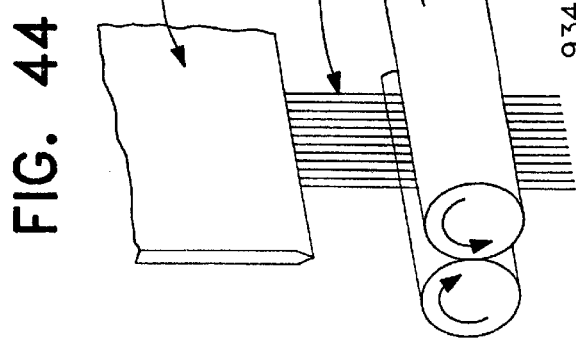
FIG. 44
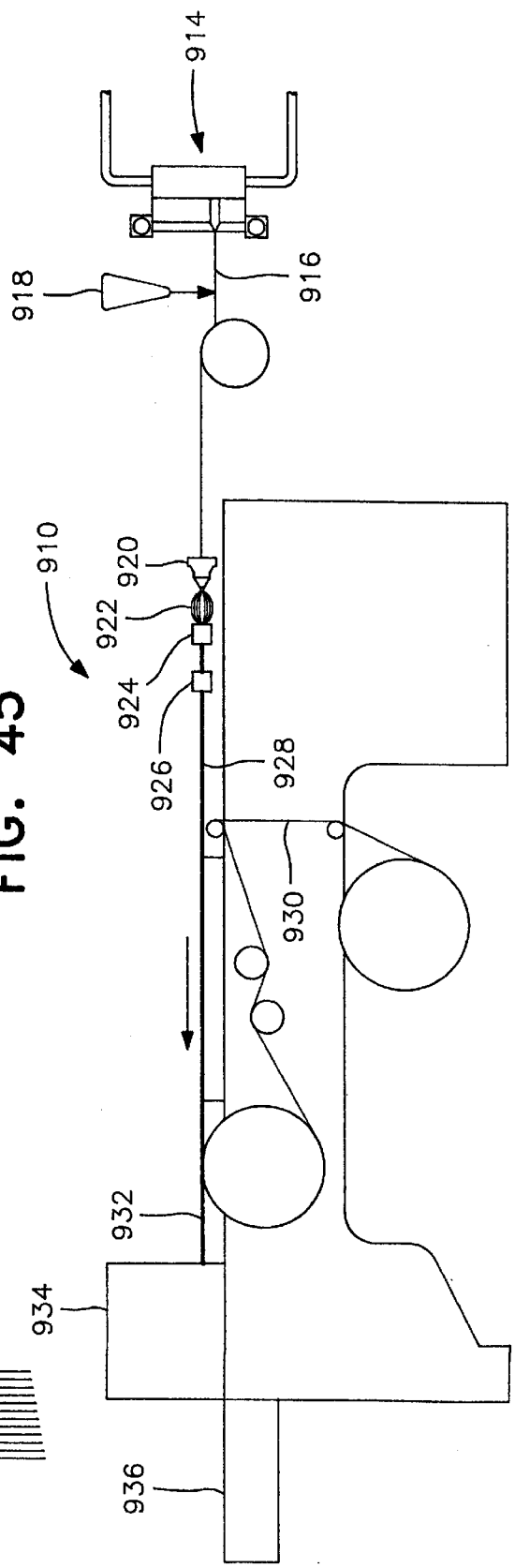

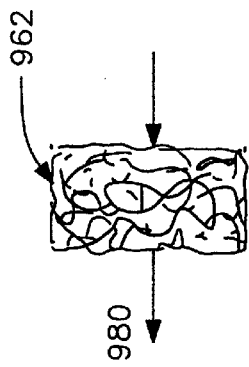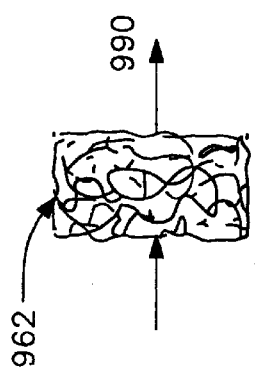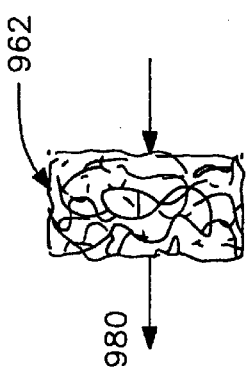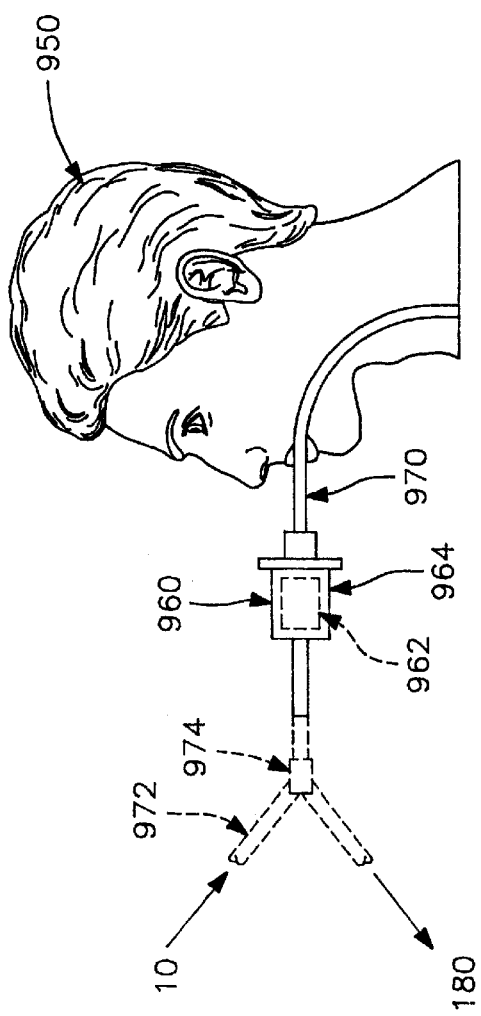

HEAT AND MOISTURE EXCHANGER COMPRISING HYDROPHILIC NYLON AND METHODS OF USING SAME

BACKGROUND OF THE INVENTION

1. Technical Field

This invention relates to a method and apparatus for extruding or spinning synthetic fibers and relates more particularly to the production of a homogeneous web of polymeric fibers wherein at least some of the fibers in the web have different characteristics from other fibers in the web, and to unique products that can be produced from such fibers. Of particular importance is the production of a homogeneously mixed fibrous web of the type described wherein at least certain of the fibers are multi-component polymeric fibers, such as sheath/core bicomponent fibers and wherein, if desired, more than one multiple-component fiber may be uniformly dispersed throughout a web of fibers, with at least the sheath of such multiple-component fibers being formed of different polymeric materials.

This invention is also concerned with unique fibrous products having diverse applications, and particularly to such products when made using the advanced homogeneous mixed fiber technology referred to above.

This invention also relates to a heat and moisture exchanger and more particularly to a gas-permeable element, preferably comprising a fibrous media which may be made by the improved mixed fiber technology discussed above and which is adapted to be warmed and to trap moisture from a patient's breath during exhalation and to be cooled and to release the trapped moisture for return to the patient during inspiration, to thereby conserve the humidity and body heat of the patient's respiratory tract during treatment of the patient requiring communication of the patient with an extracorporeal source of a gas through an artificial airway. The heat and moisture exchanger of this invention is also effective for the removal of particulate contaminants contained in the gas to protect the patient from inhaling such contaminants, and to protect the atmosphere from contaminants in the patient's exhalation.

Artificial airways are used in diverse medical procedures and take a variety of forms. The insertion of an endotracheal tube to permit a choking patient access to air provides a simple illustration. Short- and long-term connection to a mechanical ventilator when a patient requires breathing assistance is another example of a situation requiring the use of an artificial airway. Artificial airways are also necessary when infusing a patient with oxygen as is common in the intensive care unit, or an anesthetic in the surgical theater.

Regardless of the particular circumstances, the use of an artificial airway creates a common set of problems. When a person exhales normally, the mouth, nose and pharynx retain heat and moisture and tend to warm and humidify incoming air during the next breath, to thereby substantially saturate the air at body temperatures. The artificial airways in a breathing circuit of the type discussed above, bypass the natural humidification systems allowing relatively cool and dry gases, such as oxygen or an anesthetic, access to the trachea and lungs without modification impairing the ability of the respiratory tract to properly function. Dry anesthetic gases can damage cellular morphology, ciliary function and increase patient susceptibility to infection. The lack of humidity causes water to vaporize from the tracheal mucosa. Additionally, heat is lost when a cool gas is inspired, causing the mucosa to dry and secretions to thicken. The resultant difficulty in clearing the respiratory tract can produce an obstruction of the natural airway.

Thus, the inhalation of poorly humidified gases can not only cause a patient discomfort, but it can increase the risks of pulmonary damage. Moreover, the resultant heat loss through the respiratory tract may cause post-operative patient shivering and require unnecessary patient reheating during recovery.

Another complication resulting from the need to connect a patient to an extracorporeal source of gas through an artificial airway is the possibility of infecting the patient with bacterial, viral or other contaminants present in the inspired gas. Similarly, contaminants passing to the environment through the artificial airway can pollute the atmosphere. These problems are particularly important when treating infected or immno-compromised patients, or in the intensive care unit where both the patient being treated and other patients in the area are likely to be especially sensitive to the airborne transmission of pathogenic organisms.

2. Discussion of the Prior Art

Various prior art techniques are known for the production of polymeric fibers, including monocomponent fibers and multiple-component fibers of various configurations. Among such multiple-component fibers, bicomponent fibers comprising a core of one polymer and a coating or sheath of a different polymer are particularly desirable for many applications.

For example, in my prior U.S. Pat. No. 5,509,430 issued Apr. 23, 1996, the subject matter of which is incorporated herein in its entirety by reference, unique polymeric bicomponent fibers comprising a core of a low cost, high strength, thermoplastic polymer, preferably polypropylene, and a bondable sheath of a material which may be cellulose acetate, ethylene-vinyl acetate copolymer, polyvinyl alcohol, or ethylene-vinyl alcohol copolymer are disclosed for use particularly in the production of tobacco smoke filters. The bicomponent fibers produced according to the techniques of the '430 patent may be melt blown to produce very fine fibers, on the order of about 10 microns or less in diameter, in order to obtain enhanced filtration. Such products are shown to have improved tobacco smoke filtration efficiency, acceptable taste, and can be produced at a substantially lower cost than conventional tobacco smoke filters formed from fibers consisting entirely of cellulose acetate.

In my subsequent U.S. Pat. Nos. 5,607,766 issued Mar. 4, 1997, 5,620,641 issued Apr. 15, 1997, and U.S. Pat. No. 5,633,082 issued May 27, 1997, the subject matters of which are also incorporated herein in their entireties by reference, unique melt blown bicomponent fibers comprising a core of a thermoplastic material covered by a sheath of polyethylene terephthalate and methods of making same are disclosed as particularly useful in the production of elongated, highly porous elements having numerous applications. For example, such products are useful as wick reservoir elements for marking and writing instruments, that is, materials designed to take up a liquid and later controllably release the same as in an ink reservoir. Additionally, because of their high capillarity, such materials function effectively in the production of simple wicks for transferring liquid from one place to another, such as in the production of the fibrous nibs found in certain marking and writing instruments. Wicks of this sort are also useful in diverse medical applications, for example, the transport of bodily fluid by capillary action to a test site in a diagnostic device.

Products made from the bicomponent fibers of the '766, '641 and '082 patents are also shown to be useful as absorption reservoirs, i.e., as a membrane to take up and simply hold the liquid as in a diaper or an incontinence pad.

Absorption reservoirs are also useful in medical applications. For example, a layer or pad of such material may be used in an enzyme immunoassay test device where they will draw a bodily fluid through the fine pores of a thin membrane coated, for example, with monoclonal antibodies that interact with antigens in the bodily fluid which is pulled through the membrane and then held in the absorption reservoir. Such materials are also suggested, with the possible addition of a smoke-modifying or taste-modifying material, for use in tobacco smoke filters.

Polymeric fibers, in general, may be produced by a number of common techniques, oftentimes dictated by the polymer itself or the desired properties and applications for the resultant fibers. Among such techniques, are conventional melt spinning processes wherein molten polymer is pumped under pressure to a spinning head and extruded from spinneret orifices into a multiplicity of continuous fibers. Melt spinning is only available for polymers having a melting point temperature less than its decomposition point temperature, such as nylon, polypropylene and the like whereby the polymer material can be melted and extruded to fiber form without decomposing. Other polymers, such as the acrylics, cannot be melted without blackening and decomposing. Such polymers can be dissolved in a suitable solvent (e.g., acetate in acetone) of typically 20% polymer and 80% solvent. In a wet solution spinning process, the solution is pumped, at room temperature, through the spinneret which is submerged in a bath of liquid (e.g. water) in which the solvent is soluble to solidify the polymeric fibers. It is also possible to dry spin the fibers into hot air, rather than a liquid bath, to evaporate the solvent and form a skin that coagulates. Other common spinning techniques are well known and do not form a critical part of the instant inventive concepts.

After spinning, the fibers are commonly attenuated by withdrawing them from the spinning device at a speed faster than the extrusion speed, thereby producing fibers which are finer and, depending upon the polymer, possibly, more crystalline in nature and, thereby, stronger. The fibers may be attenuated by taking them up on rotating nip rolls or by melt blowing the fibers, that is, contacting the fibers as they emanate from the spinneret orifices with a fluid, such as air, under pressure to draw the same into fine fibers, commonly collected as an entangled web of fibers on a continuously moving surface, such as a conveyor belt or a drum surface, for subsequent processing.

As described in my aforementioned patents, the extruded fibrous web may be gathered into a sheet form which may be pleated to increase the surface area for certain filtering applications. Alternatively, the web of fibers may be gathered together and passed through forming stations, such as steam treating and cooling stations, which may bond the fibers at their points of contact to form a continuous rod-like porous element defining a tortuous path for passage of a fluid material therethrough.

While earlier techniques and equipment for spinning fibers have commonly extruded one or more polymer materials directly through an array of spinneret orifices to produce a web of monocomponent fibers or a web of multiple-component fibers, recent development incorporate a pack of disposable distribution or spin plates juxtaposed to each other, with distribution paths being etched into upstream and/or downstream surfaces of the plates to direct streams of one or more polymer materials to and through spinneret orifices at the distal end of the spinning system. These techniques are embodied, for example, in Hills U.S. Pat. No. 5,162,074 issued Nov. 10, 1992, the subject matter of which is incorporated herein in its entirely by reference, and provide a reasonably inexpensive way to manufacture highly sophisticated spinning equipment and to produce a high density of continuous fibers formed of more than one polymeric material. Hills recognizes the production of multiple-component fibers, such as bicomponent fibers, wherein the components adhere to each other in a durable fashion, or, alternatively, are poorly adhering so that the components may be split apart to increase the effective fiber yield from each spinneret opening and to produce finer fibers from the individual components.

Although Hills and others provide relatively inexpensive, even disposable, distribution plates capable of spinning a high density of identical fibers, which may include separable segments of different polymeric materials, and the production of a web of mixed fibers, i.e., fibers having different physical and/or chemical characteristics, is broadly referred to in the literature, to my knowledge the prior art fails to recognize the advantages of directly spinning a homogeneous or uniform mixture of fibers from a spinning device, wherein the fibers extruded from certain of the spinneret orifices in the same element have different characteristics from the fibers extruded from other spinneret orifices in that element. Moreover, the techniques and equipment currently commercially available are not adapted to produce such a homogeneous web of mixed fibers, most especially, a uniformly distributed mixture of monocomponent and multiple-component fibers, or even a uniform mixture of different multiple-component fibers, e.g., where adjacent fibers in the web have different polymeric coatings such as alternating bicomponent fibers having a common core-forming polymer and different sheath-forming polymers.

Although fibrous products, including the unique melt-blown bicomponent fibers of my '430, '766, '641 and '082 patents discussed above, have significant commercial applications, the functional properties of the available products are limited by the inability of prior art technology to produce uniform and consistent webs of mixed fibers of differing chemical and/or physical characteristics. To the extent that the prior art is capable of producing mixed fibrous webs, the apparatus and techniques for doing so are generally inadequate for commercial application and/or are unable to provide reproducible, highly homogeneous, mixtures of diverse fibers from the same set of spinneret orifices.

With an improved ability to produce mixed fiber webs of substantially complete uniformity, improved functional properties can be afforded in a variety of fibrous products, whether they are intended to for use as high efficiency filters such as are required in electric dust collection devices and power plants, coalescent-type filters such as those used to separate water from aviation fuel, wicking products such as may be used for ink transfer in marking and writing instruments or as medical wicks, or in similar liquid holding and transferring applications, or in diverse other fields.

With respect to a particular application of the improved technology of this invention, that is, in the production of heat and moisture exchangers and high efficiency particulate air filters for use in a breathing circuit requiring an artificial airway, various prior art devices are commercially available. Oftentimes, however, separate devices are necessary to conserve the humidity and body heat of the patient's respiratory tract and to filter undesirable constituents from a gas being inhaled by the patient, or from the patient's breath exhaled during such treatments. Although some devices are available which incorporate media capable of performing all of these functions, it is not uncommon in such devices for particular properties to be compromised in order that other properties can be enhanced. The availability of a device capable of maximizing both heat and moisture exchange and filtration in an economic manner would be most desirable.

Early attempts to humidify a patient's respiratory tract and thereby reduce heat loss during short or long-term mechanical ventilation or the like, utilized electrically heated, water-filled humidifiers to add water vapor to the airway. This approach produced almost as many problems as it solved. The water level and temperature of the water vapor required constant monitoring. Further, particular difficulty was experienced in controlling the delivery of the small volumes of moisture needed for children or infants. Condensation of the water vapor could plug the small airways and, in extreme situations, even cause drowning. Additionally, the development of deposits in the humidifier reservoir often contaminated the moisture, thereby damaging the equipment and possibly harming the patient. The presence of such contaminants simply increased the need for effective filtration.

More recently, regenerative humidifiers or "artificial noses" have been developed as safe and effective alternatives to overcome many of the foregoing problems with heated water bath humidifiers. Such units are commonly referred to as heat and moisture exchangers (HMEs) because they function much in the same way as the patient's natural resources, that is, they capture the moisture and heat as the patient exhales and return them to the patient during the next breath.

HMEs are passive, requiring no outside source of moisture or power. They are placed in line with the artificial airway and are provided with a media producing a large surface area for the exchange of heat and moisture The HME media is warmed as humidity in the patient's breath condenses during exhalation, is cooled during inhalation as it gives up heat and moisture vapor to the inspired gases, and the process is repeated as the patient breathes in and out.

Attempts have been made to increase the hygroscopicity of the HME media to thereby directly absorb moisture from exhaled gases, whereby the media retains more moisture than would have been collected from condensation alone to thereby improve the HME output. Further, since the moisture held by the hygroscopic media is absorbed and not condensed, vaporative cooling of the HME is limited when this moisture is released during inhalation.

While the concept is technically sound, the particular hygroscopic materials commercially available are either inadequate or undesirable for use as HME media. Additives such as salts, e.g., lithium chloride, or glycerin provide advantageous hygroscopicity to HME media, but can contaminate and even interact with gases passing through such media during inspiration by the patient. Provision of an HME media capable of attracting and holding additional moisture from a patient's breath during exhalation without the need for extraneous chemicals is important to the safe and effective operation of an HME in auxiliary breathing equipment.

A number of criteria are particularly important in the design of an HME for medical applications. Low thermal conductivity of the heat and moisture exchange media increases the temperature differential across the HME, improving its efficiency. A low pressure drop across the HME is essential to minimize effort during normal breathing or mechanical ventilation. An HME must also be relatively lightweight since it is to be supported at a tracheotomy, endotracheal or nasotracheal site in most applications. The HME media should be disposable or easily sterilized to minimize costs in maintaining the breathing circuit. Finally, the HME media should be effective without the need for chemical additives that could affect the treated gases, and the media should not release any particulate matter, thereby protecting the patient and the environment as well as the equipment with which the HME is associated against contamination.

In summary, the HME must efficiently, inexpensively and safely provide adequate heat and moisture, preferably, to enable a single unit to effectively conserve the humidity and body heat of the patient's respiratory tract and, if possible, concomitantly filter gases passing therethrough to remove particulate contaminants, thereby avoiding the need for redundant units.

OBJECTS AND SUMMARY OF THE INVENTION

It is, therefore, a primary object of this invention to provide a unique fiber spinning process and apparatus for use therewith which feeds polymer materials from independent sources through mutually separated distribution paths to an array of spinneret orifices, wherein the fibers extruded from selected ones of the spinneret orifices have different characteristics from fibers extruded from other spinneret orifices.

Consistent with the foregoing object, adjacent fibers may be formed of the same or different polymers, may have different color, shape or texture and/or may have different denier. Moreover, according to a preferred feature of this invention, some fibers in the web may be monocomponent and others multiple-component. Thus, this invention enables the simultaneous extrusion of monocomponent fibers side-by-side with bicomponent fibers having a core of the monocomponent polymer material and a sheath of a different polymer material. Alternatively, bicomponent fibers with a common core-forming polymer and different sheath-forming polymer materials may be formed side-by-side and uniformly distributed throughout the same web of fibers as it is extruded.

Another object of this invention is the provision of a spinning device comprising a pack of distribution or spin plates defining separated distribution paths for receiving polymeric materials from multiple independent sources and delivering each of such materials to selected spinneret orifices of an array of spinneret orifices to produce a uniform blend of fibers of differing characteristics from the individual spinneret orifices.

A further object of this invention is the provision of a pack of distribution plates wherein independent distribution paths may be relatively inexpensively formed in one or both surfaces by any of a variety of techniques, including etching, milling or electrical discharge machining and the like, such that the plates can be reused or replaced from time to time.

A still further object of this invention is the provision of a pack of spin plates of the type described, wherein a line of spinneret orifices is defined in a single plate as through-holes parallel to the plane of the plate, such that the fibers are totally surrounded by a seamless forming surface as they are extruded, thereby precluding polymer leakage and non-uniformity in the resultant fibers.

Further objects of this invention reside in the uniquely homogeneous nature of the mixture of polymeric components and/or fibers of different characteristics in a web of fibers, enabling products made therefrom to have unusual chemical and/or physical properties. Consistent with this object, for example, the web of fibers can incorporate selected fibers having surface characteristics capable of bonding different fibers into a self-sustaining porous matrix defining a tortuous path for passage of a fluid material therethrough. Certain fibers in the mixture may provide the resultant product with increased strength, while other components may provide special characteristics, such as wicking, absorption, coalescing, filtration, heat and/or moisture exchange, and the like.

A still further object of the instant inventive concepts is the provision of products incorporating the unique web of mixed fibers such as wick reservoirs, including ink reservoirs and marking and writing instruments incorporating the same, filtering materials, including tobacco smoke filters and filtered cigarettes formed therefrom, wicks for transporting liquid from one place to another by capillary action, including fibrous nibs for marking and writing instruments and capillary wicks in medical applications designed to transport a bodily fluid to a test site in a diagnostic device and absorption reservoirs, membranes for taking up and holding liquid as in a diaper or an incontinence pad, or in medical applications such as enzyme immunoassay diagnostic test devices wherein a pad of such material will draw a bodily fluid through a thin membrane and hold the fluid pulled therethrough.

Yet another important object of this invention to provide a unique heat and moisture exchanger which overcomes the aforementioned and other disadvantages of prior art HMEs designed for use in artificial airways. Most importantly, the instant invention provides an HME media which is highly efficient, without the need for chemical additives that might otherwise contaminate either the gas inspired by the patient, the patient's breath exhaled through the HME to the atmosphere, or the airway tubing or valves or other equipment forming part of the breathing circuit.

A still further object of this invention is the provision of an HME which is relatively lightweight, has a low thermal conductivity and a low pressure drop to increase the efficiency of the HME and decrease the difficulty in use of same in an artificial airway.

Consistent with these objects, the instant invention provides an HME, adapted to be interposed in both inspiratory and expiratory airways for oxygen infusion, anesthesia, ventilation and other such medical applications, which includes a gas-permeable element, preferably a fibrous media, comprised of a hydrophilic nylon polymer which has been surprisingly found to be more effective than other HME media, including hygroscopic media currently available, in capturing moisture and heat from a patient's breath during exhalation, and cooling and releasing the trapped moisture for return to the patient during inspiration, without the need for chemical additives.

Another object of this invention is the provision of an HME comprising hydrophilic nylon polymeric fibers, especially fine fibers, bonded at their points of contact into a three-dimensional porous element defining a tortuous path for passage of a gas therethrough to increase its heat and moisture transfer effectiveness and, additionally, to remove undesirable particulate contaminants from the gases passing therethrough, thereby protecting the patient and the medical workers from cross-contamination, isolating the breathing circuit from the patient, and extending the useful life of mechanical ventilation equipment. The filtration effectiveness of an HME according to this invention finds particular use in an expiratory line to prevent undesirable contaminants from being expelled into the environment and on a main line to filter incoming gas.

Yet another object of this invention is the provision of an HME wherein the filter media includes bicomponent fibers comprising a sheath of the hydrophilic nylon polymer and a core of a different and less expensive polymer, such as polypropylene, enabling the media to be readily replaced between uses in a cost-effective manner.

Most preferably, it is an important object of this invention to provide an HME wherein the media is formed using the improved mixed fiber technology of this invention from a substantially uniform mixture of bicomponent fibers, some of which comprise a hydrophilic nylon polymer sheath, and others of which comprise a sheath of a thermoplastic polymer having a melting point lower than the hydrophilic nylon polymer, such as a polyester, to thereby provide an effective bonding agent for the hydrophilic nylon polymer fibers, with all of the bicomponent fibers having a common, and relatively inexpensive, core-forming polymer.

Upon further study of the specification and the appended claims, additional objects and advantages of this invention will become apparent to those skilled in the art.

BRIEF DESCRIPTION OF THE DRAWINGS

A better understanding of the present invention, as well as other objects, features and advantages thereof, will become apparent upon consideration of the detailed description herein in connection with the accompanying drawings, wherein like reference characters refer to like parts.

Reference in the description of the drawings and the subsequent detailed description of the preferred embodiments to "upstream" and "downstream" relates to the direction of initial flow of the fiber-forming polymers into the die assembly.

FIG. 5 is an enlarged detailed view of the portion of FIG. 3 within the circle A.

FIG. 6 is a view similar to FIG. 3, but taken from a different angle.

FIG. 7 is an enlarged detailed view of the portion of FIG. 6 within the circle B.

FIG. 10 is an enlarged detailed view of the portion of FIG. 8 within the circle C.

FIG. 16 is an upstream plan view of a portion of the right distribution plate.

FIG. 17 is a downstream plan view thereof.

FIG. 18 is a side elevational view thereof, with hidden parts shown in dotted lines.

FIG. 19 is an upstream perspective view of a portion of the right distribution plate.

FIG. 20 is a downstream perspective view thereof.

FIG. 21 is an upstream plan view of a portion of the left distribution plate.

FIG. 22 is a downstream plan view thereof.

FIG. 23 is a side elevational view thereof, with hidden parts shown in dotted lines.

FIG. 24 is an upstream perspective view of a portion of the left distribution plate.

FIG. 25 is a downstream perspective view thereof.

FIG. 31 is a fragmentary upstream plan view of the distribution plate assembly of the spinning device of this embodiment of the instant invention, with hidden parts shown in dotted lines for illustrative clarity.

FIG. 32 is an enlarged cross-sectional view taken along lines 32—32 FIG. 31, illustrating the path of the core-forming polymer and the first sheath-forming polymer in the production of alternating sheath/core bicomponent fibers with the same core-forming polymer and different sheath-forming polymers according to this embodiment.

FIG. 33 is a view similar to view 32, but taken along lines 33—33 of FIG. 31, illustrating the path of the core-forming polymer and the second sheath-forming polymer.

FIG. 34 is an exploded perspective view of the distribution plates only of another embodiment of a spinning device according to the instant inventive concepts adapted to produce a homogeneous web of different monocomponent fibers from two independent sources of polymer, as seen from the upstream side.

FIG. 36 is an assembled upstream plan view of the distribution plates illustrated in FIG. 34, with hidden parts shown in dotted lines for illustrative clarity.

FIG. 37 is a cross-sectional view taken along lines 37—37 of FIG. 36 showing the path of one of the polymers through the distribution plates.

FIG. 38 a cross-sectional view taken along lines 38—38 of FIG. 36 showing the path of the other polymer through the distribution plates.

FIG. 44 is a schematic view of a web of fibers extruded from a spinning device according to this invention fed into the nip of a pair of rotating take-up rollers.

FIG. 45 is a schematic view of one form of a process line for producing porous rods from a web of mixed fibers according to the present invention.

FIG. 46 is an enlarged schematic view of a melt blown die portion which may be used in the processing line of FIG. 45.

FIG. 47 is a schematic view illustrating a breathing circuit wherein an HME according to the instant inventive concepts is interposed in an artificial airway, the use of a "Y" connection being shown in dotted lines for connection of the artificial airway to incoming and/or outgoing lines; and FIGS. 48a–48c schematically illustrate the passage of a gas through the media of an HME according to the instant inventive concepts during a normal breathing cycle.

Like reference characters refer to like parts throughout the several views of the drawings.

DETAILED DESCRIPTION OF THE PREFERRED EMBODIMENTS

Figure 1:
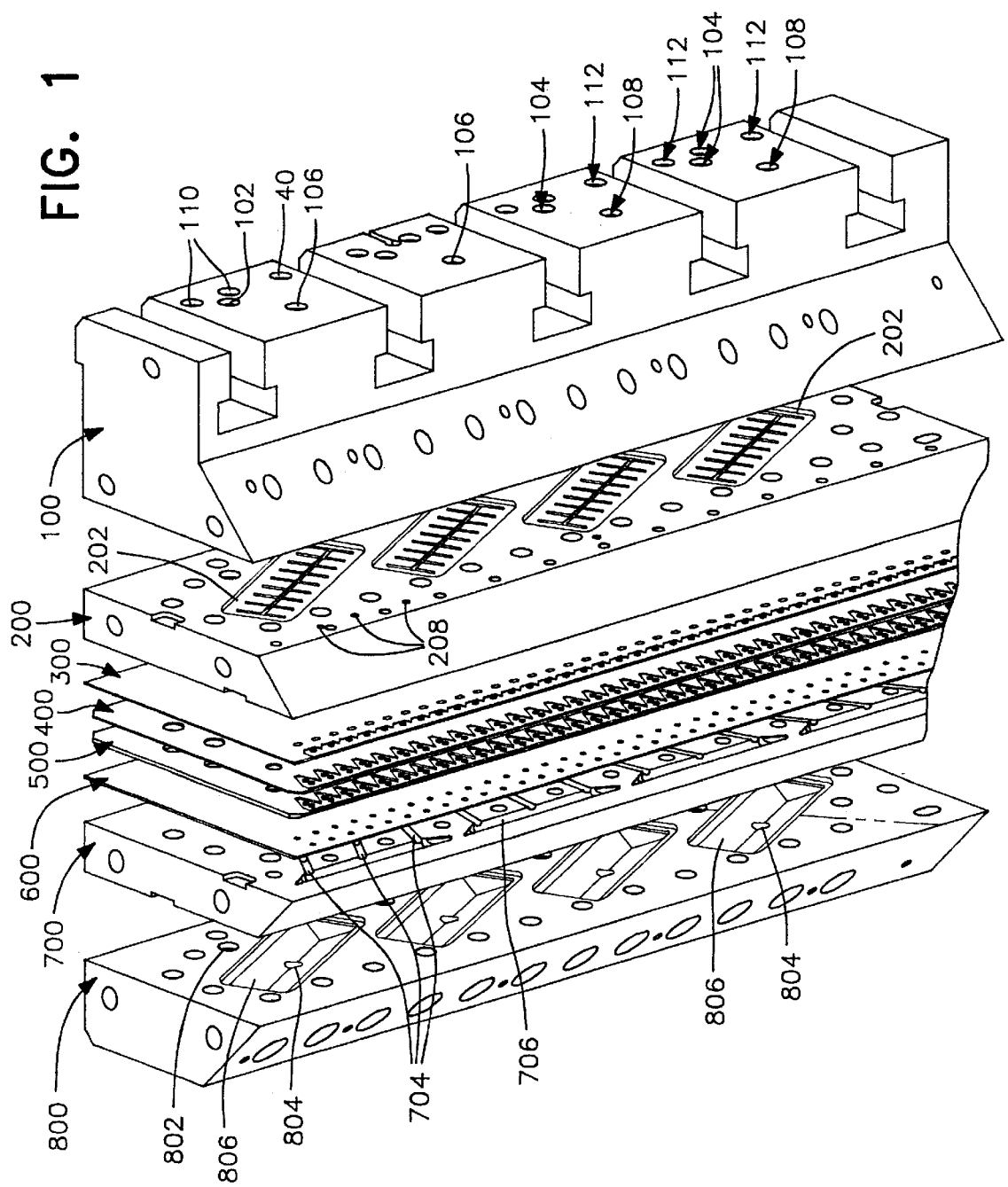
FIG. 1 is an exploded perspective view of the principal elements of a spinning device according to the instant inventive concepts designed to produce a homogeneous web of sheath/core bicomponent fibers wherein all of the fibers share the same core-forming polymer and alternate fibers having different sheath-forming polymers.

For simplicity, in illustrating the improved mixed fiber-forming apparatus of this invention, individual openings or distribution paths are not necessarily repeated in every view of each element in the drawings. It is to be understood, in any event, that the relative size of the elements, the numbers and shapes of the openings and/or cutouts forming the distribution paths for the various fiber-forming polymers as well as the number of spinneret openings shown in the drawings are illustrative and not limiting on the instant inventive concepts.

Also, although the techniques and apparatus disclosed herein are equally applicable to melt spinning, solution spinning and other conventional spinning techniques, for ease of understanding, the following description of the preferred embodiments will be primarily directed to the use of melt spun polymers.

Referring now to the drawings, and more particularly to FIGS. 1–33, the principal elements of a preferred die assembly for a spinning device according to the instant inventive concepts adapted to produce a homogeneous mixture of bicomponent fibers sharing a common core-forming polymer and comprising different sheath-forming polymers includes, starting from the upstream end (the right in FIG. 1), a mounting block 100, a right-hand nozzle 200, a distribution plate system comprising a secondary right distribution plate 300, a right distribution plate 400, a left distribution plate 500, and a secondary left distribution 600, with a left-hand nozzle 700 and a clamp block 800 on the downstream end. Note particularly FIGS. 1 and 2. Obviously, in use, the illustrated elements will be secured together by bolts or the like (not shown) to preclude polymer leakage in any conventional manner.

The core-forming polymer and the two sheath-forming polymers are fed from independent sources through melt pumps (not shown) to enter the die assembly through inlet openings in the mounting block 100. In FIG. 1, the core-forming polymer enters the mounting block 100 through openings 102 in the direction of arrows 104; the first sheath-forming polymer enters the mounting block 100 through openings 106 in the direction of arrows 108; and the second sheath-forming polymer enters the mounting block 100 through openings 110 in the direction of arrows 112.

The passage of the core-forming polymer through the die assembly will now be considered in detail. From the mounting block 100, the core-forming polymer passes straight through aligned openings in all of the die plates in one interrupted stream until it enters hole 802 of clamp block 800. The core-forming polymer then reverses direction within the clamp block 800 (not shown), returns through openings 804 to collect in cutouts 806 in the upstream side of the clamp block 800. See FIG. 1.

Figure 2:
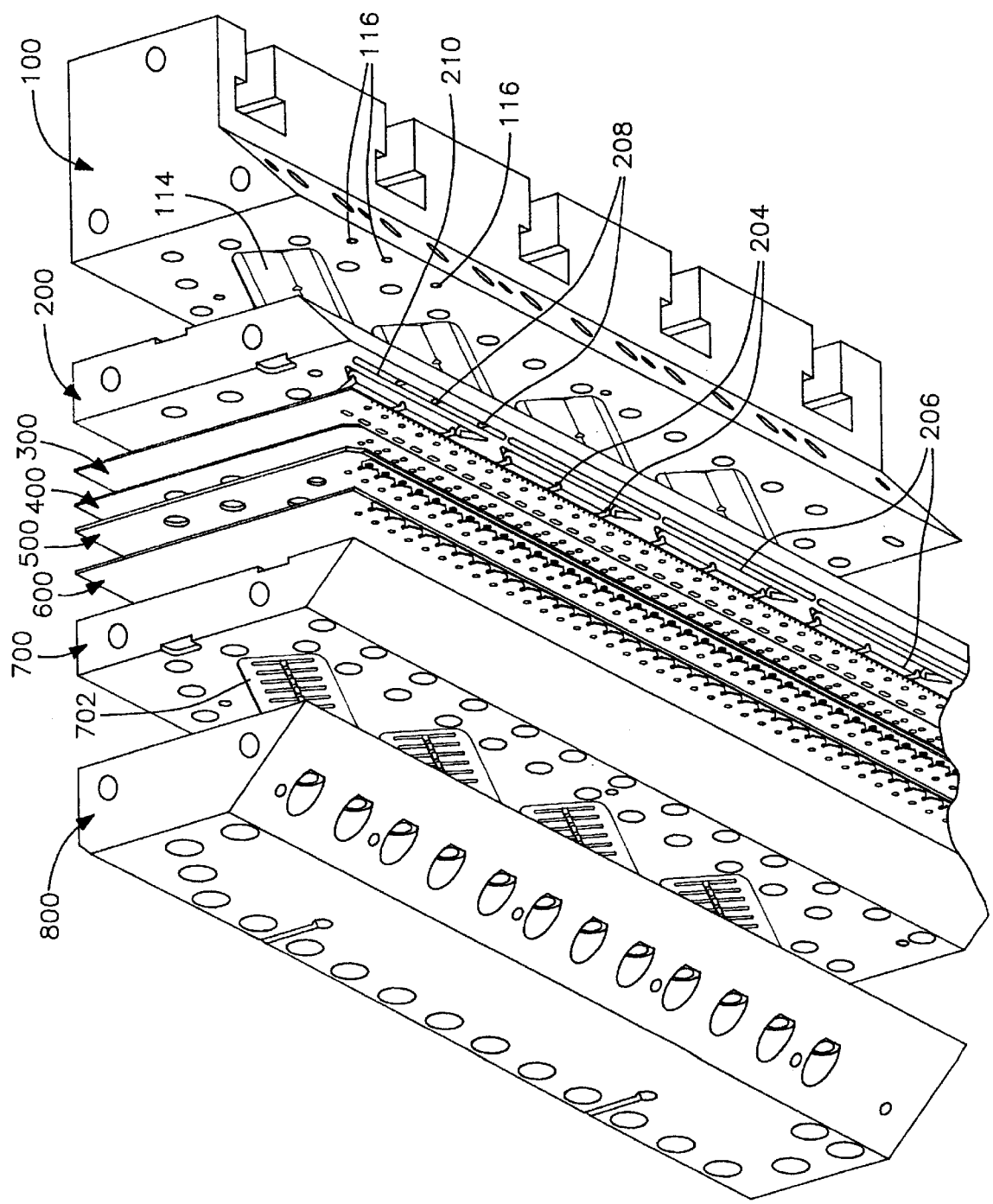
FIG. 2 is a view similar to FIG. 1 looking in the opposite direction.
Figure 4:
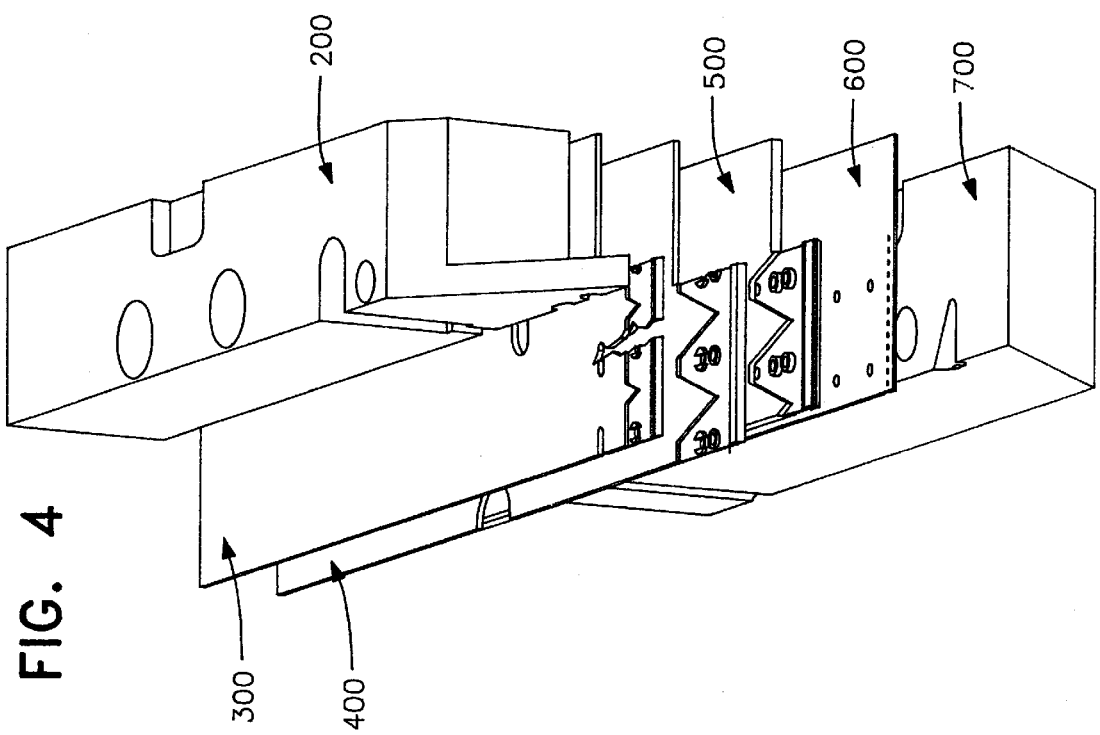
FIG. 4 is an exploded view of the elements shown in FIG. 3.
Figure 3:
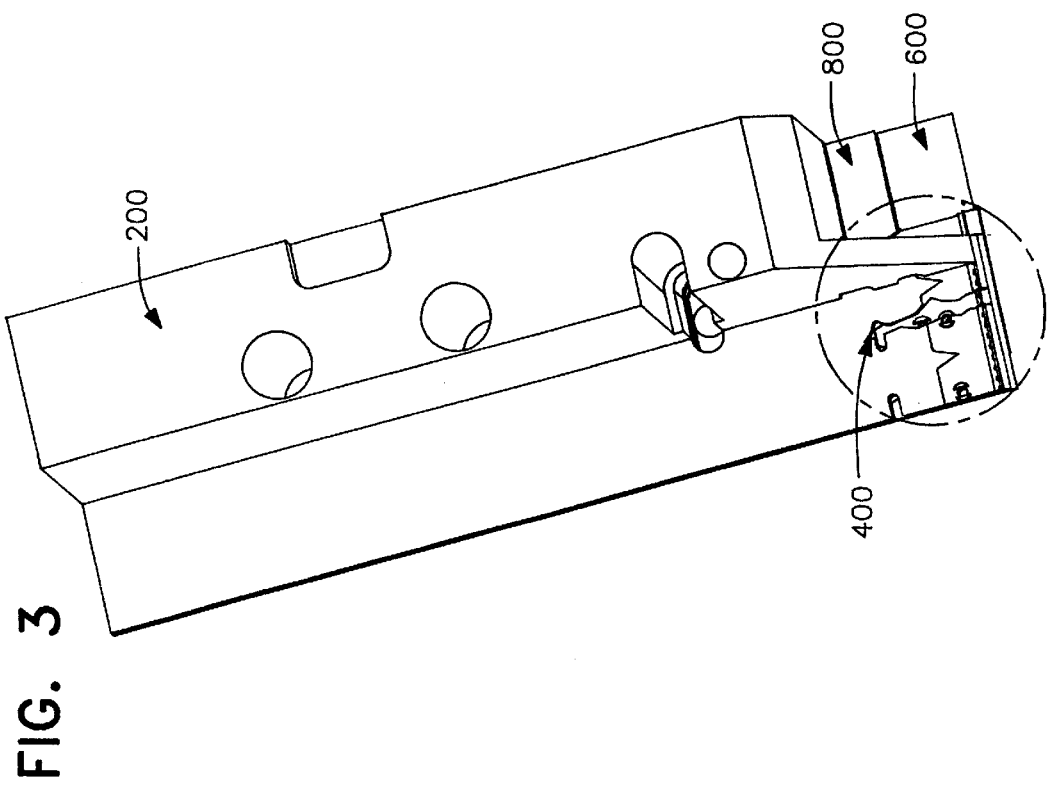
FIG. 3 is an assembled perspective view of portions of the elements shown in FIG. 1, with parts being broken away for illustrative clarity.
Figure 9:
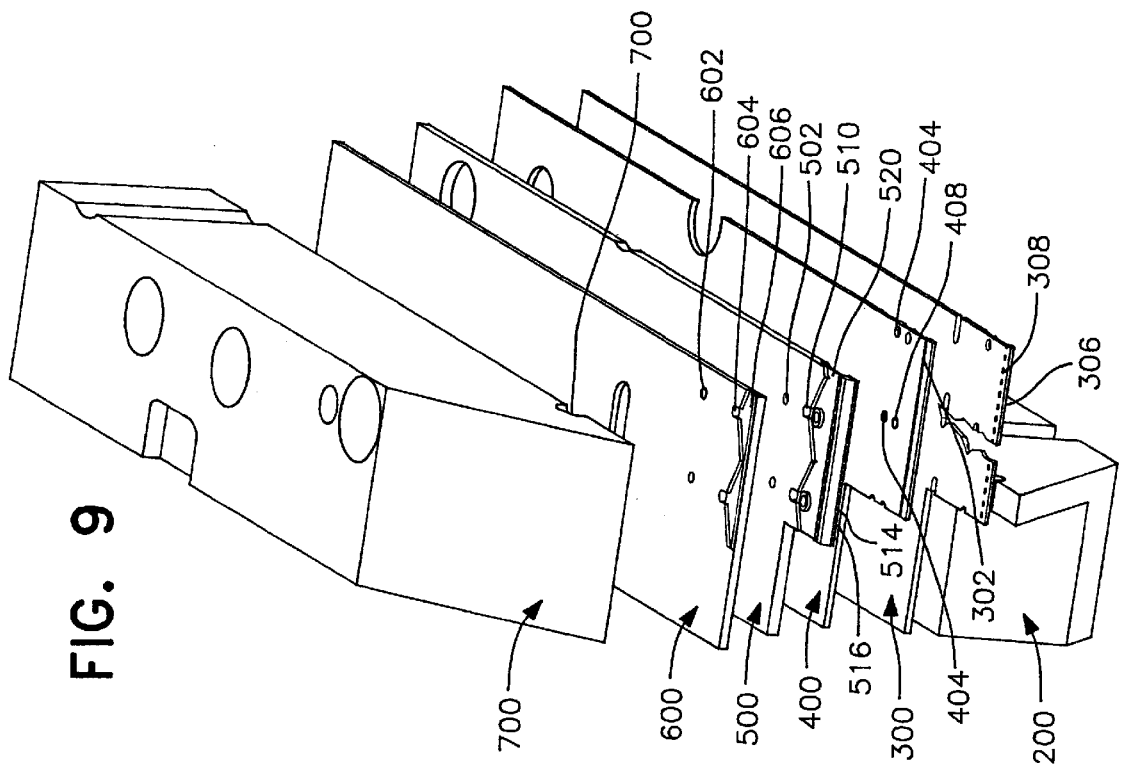
FIG. 9 is an exploded view of the elements shown in FIG. 8.
Figure 8:
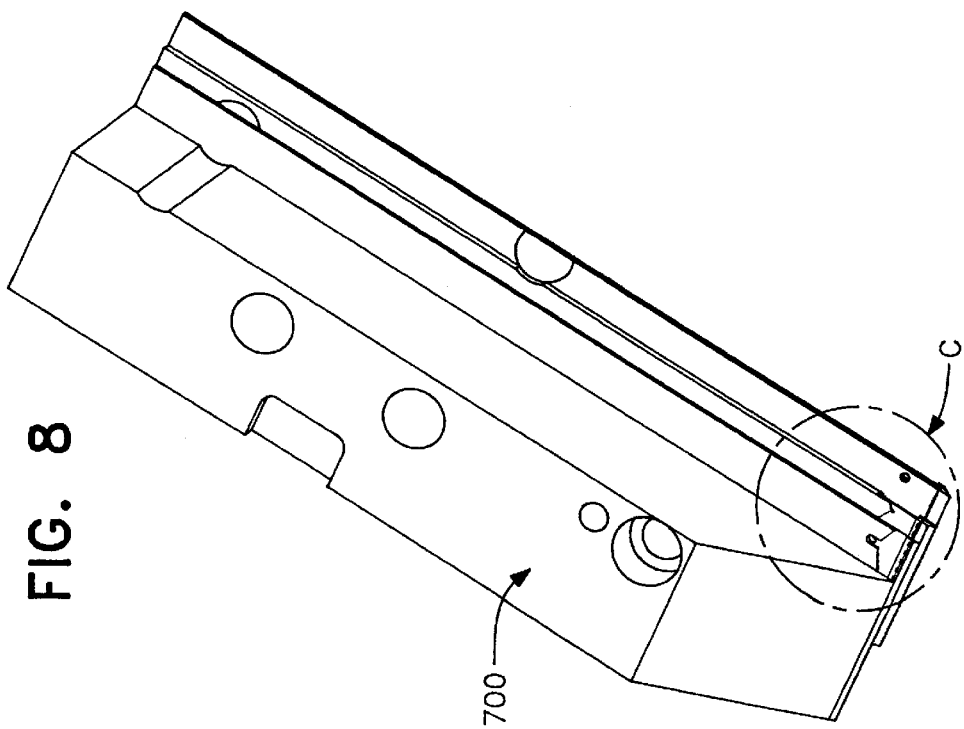
FIG. 8 is a perspective view similar to FIG. 3, but looking from the opposite side of the assembly.
Figure 12:
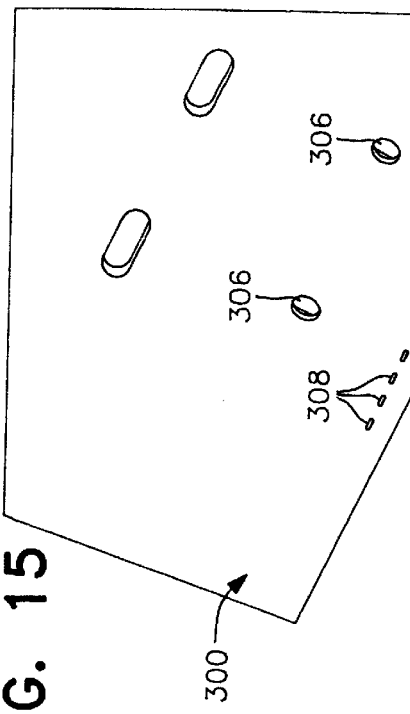
FIG. 12 is a downstream plan view thereof.
Figure 13:
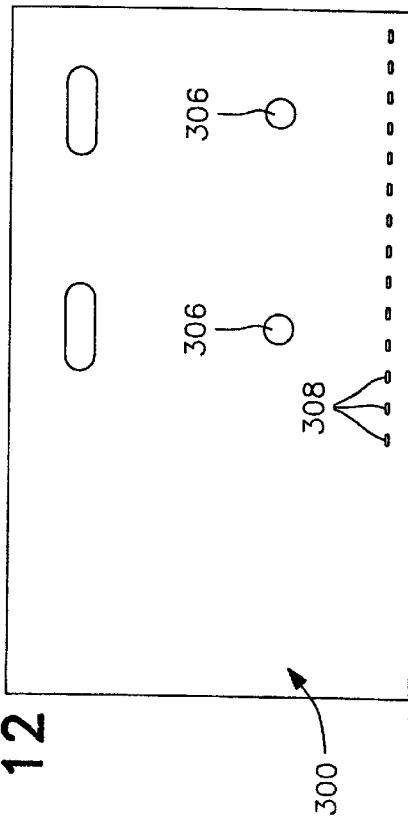
FIG. 13 is a side elevational view thereof, with hidden parts shown in dotted lines.
Figure 15:
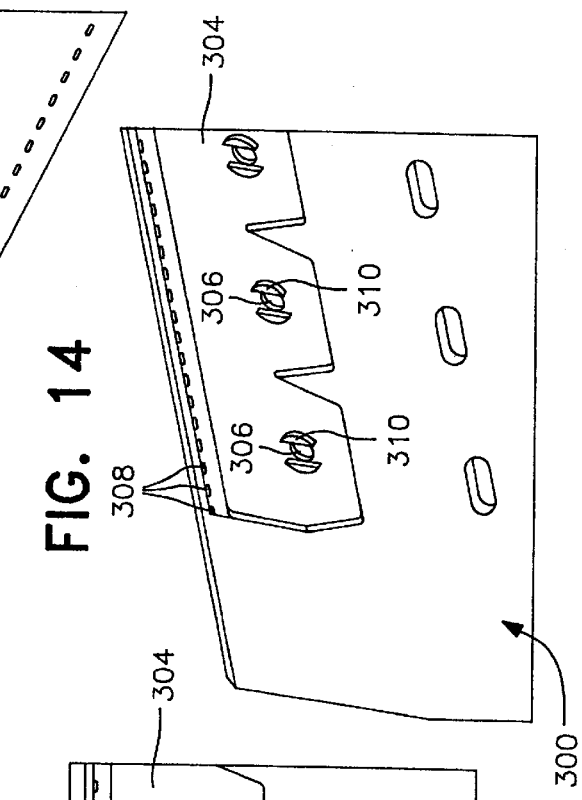
FIG. 15 is a downstream perspective view thereof.
Figure 14:
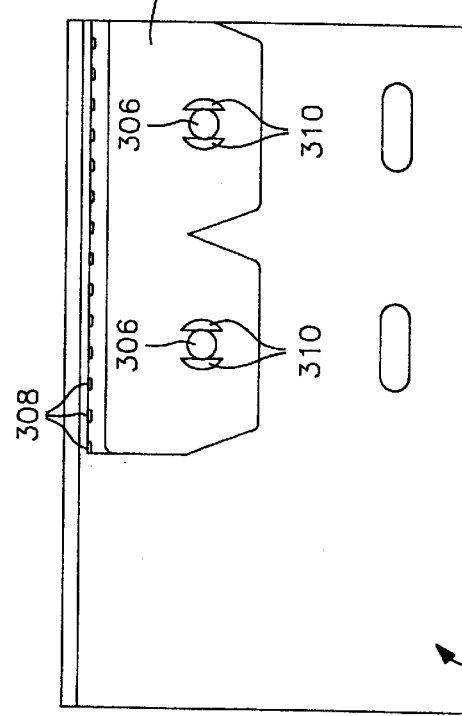
FIG. 14 is an upstream perspective view of a portion of the secondary right distribution plate.
Figure 11:
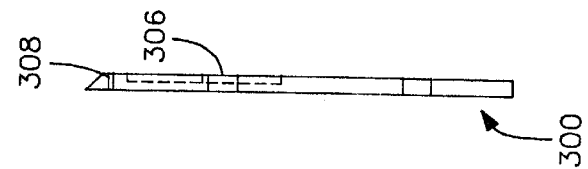
FIG. 11 is an upstream plan view of a portion of the secondary right distribution plate.
Figure 27:
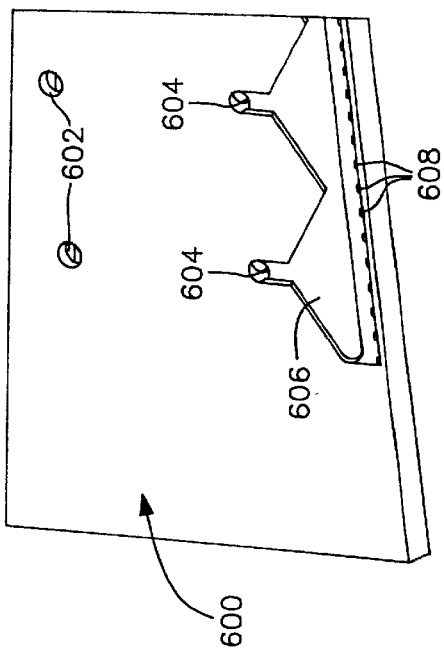
FIG. 27 is a downstream plan view thereof.
Figure 30:
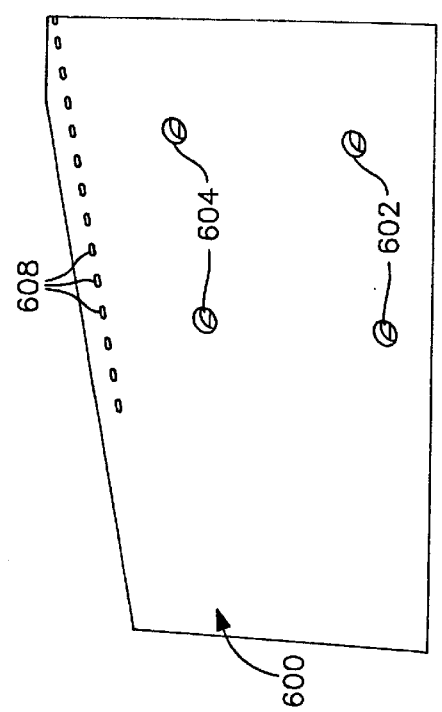
FIG. 30 is a downstream perspective view thereof.
Figure 26:
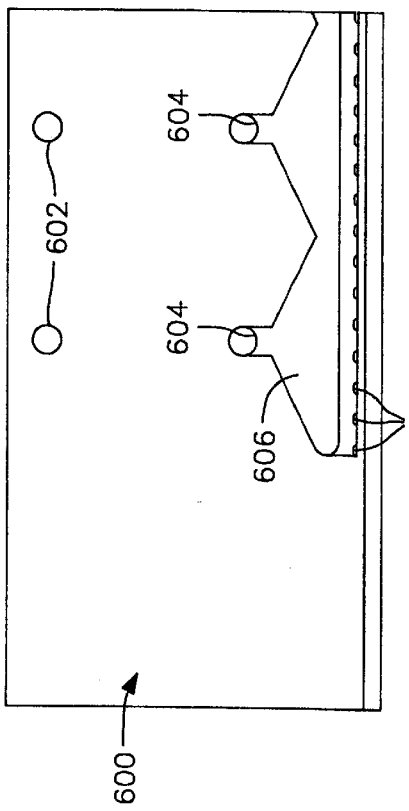
FIG. 26 is an upstream plan view of a portion of the secondary left distribution plate.
Figure 29:
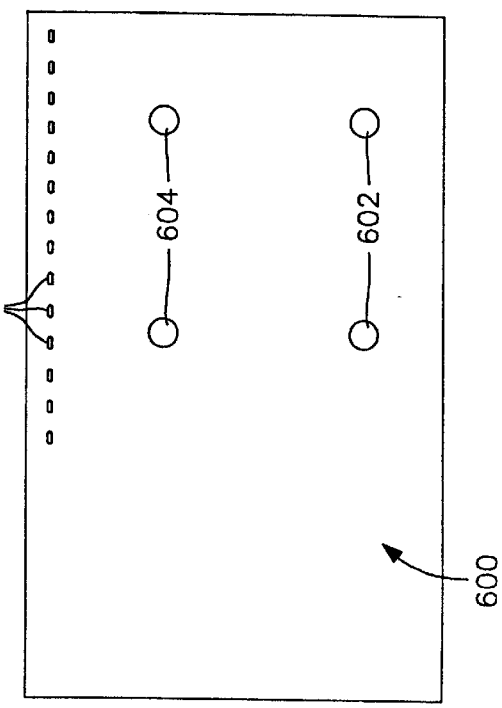
FIG. 29 is an upstream perspective view of a portion of the secondary left distribution plate.
Figure 28:
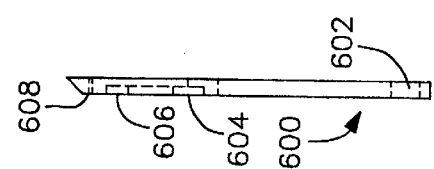
FIG. 28 is a side elevational view thereof, with hidden parts shown in dotted lines.
Figure 35:
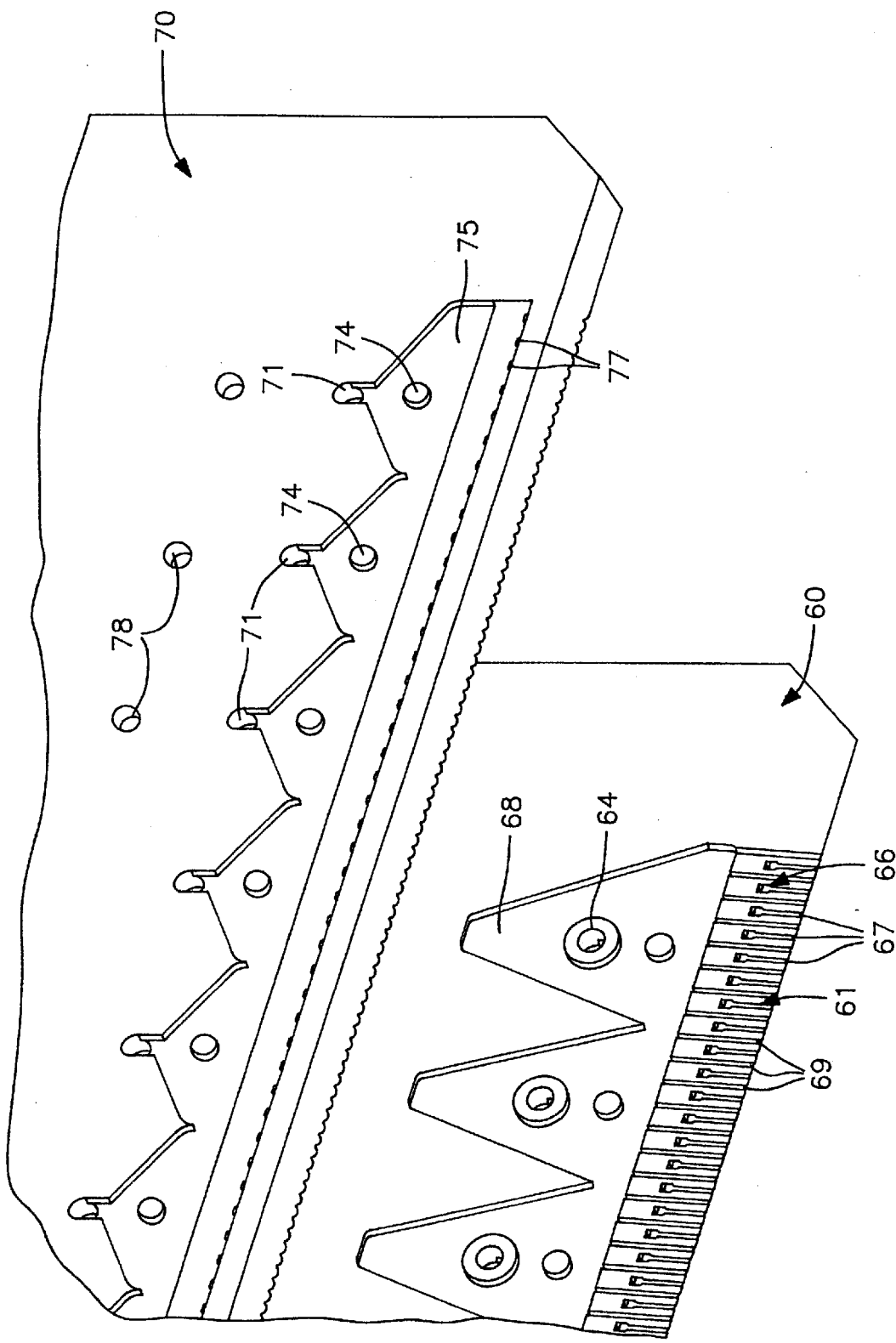
FIG. 35 is a view of the elements illustrated in FIG. 34, taken from the downstream side.
Figure 39:
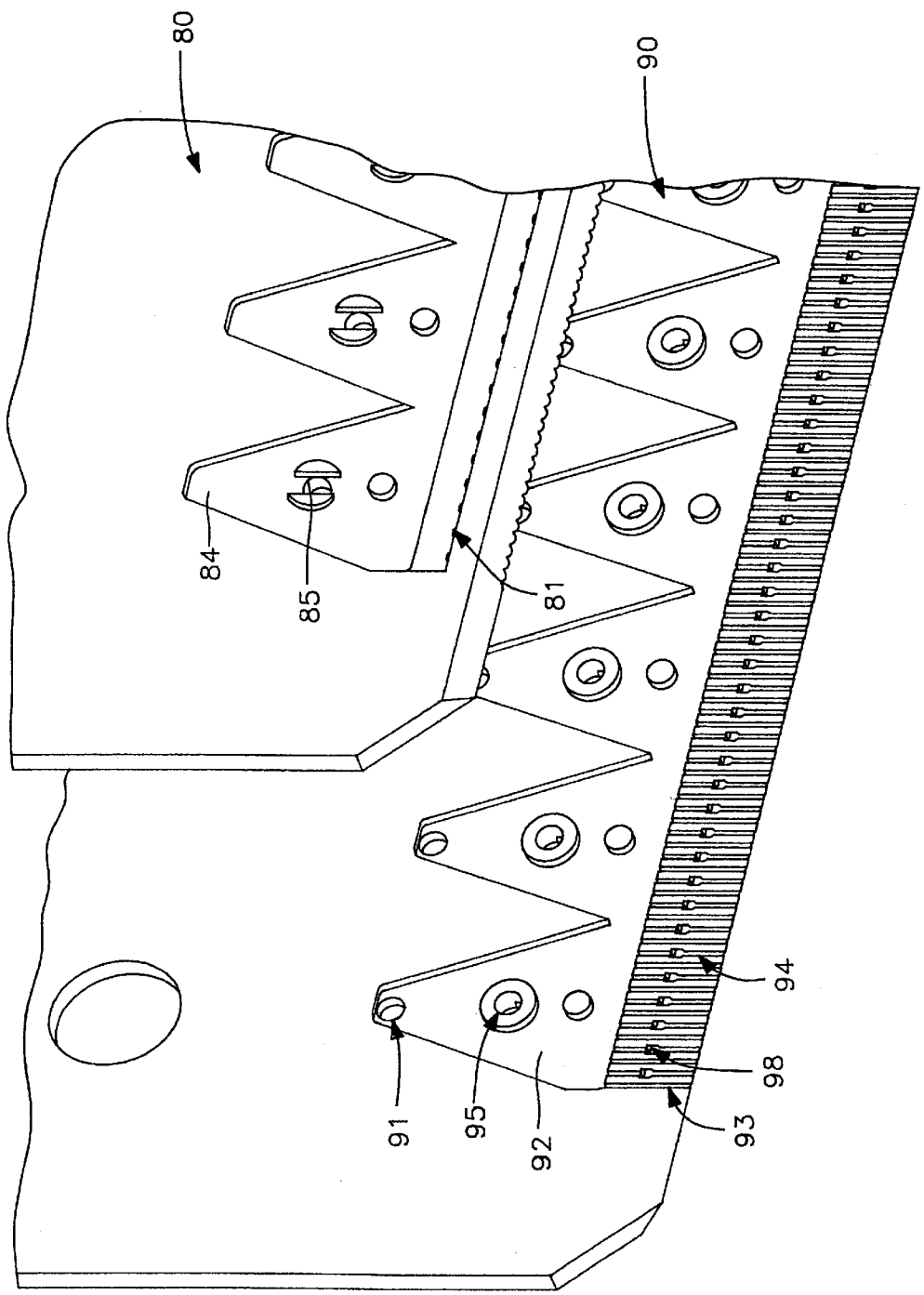
FIG. 39 is an exploded perspective view of the distribution plates only of yet another embodiment of a spinning device according to the instant invention adapted to produce a homogeneous web of fibers comprising bicomponent sheath/core fibers and monocomponent fibers formed from the core-forming polymer of the bicomponent fibers, as seen from the upstream side.
Figure 40:
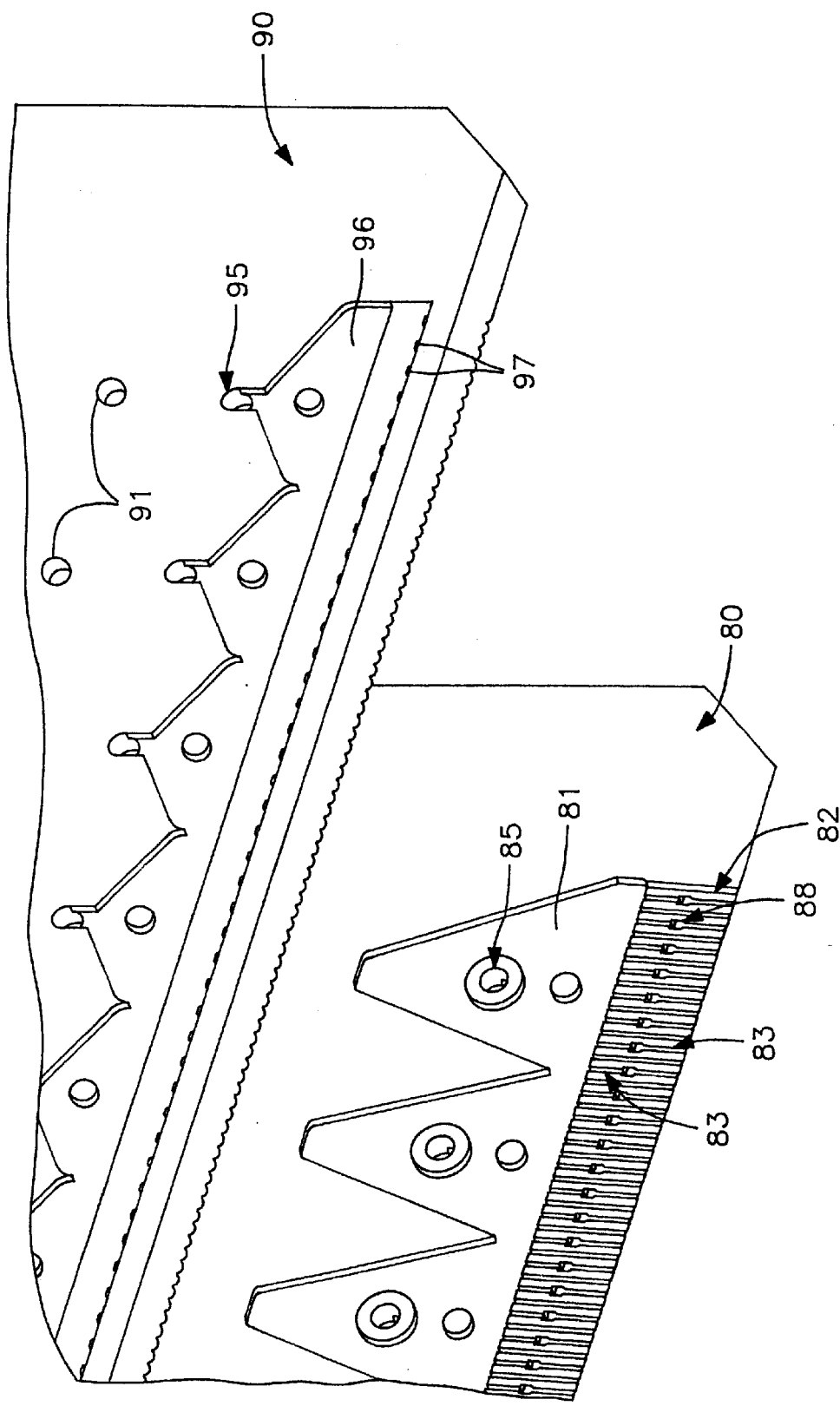
FIG. 40 is a view of the elements illustrated in FIG. 39, taken from the downstream side.
Figure 43:
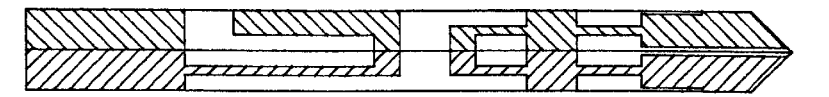
FIG. 43 a cross-sectional view taken along lines 43—43 of FIG. 41 showing the path of the core-forming polymer through the distribution plates to form the monocomponent fibers.
Figure 42:
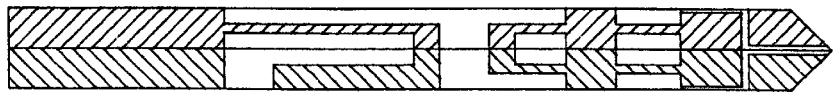
FIG. 42 is a cross-sectional view taken along lines 42—42 of FIG. 41 showing the path of the core-forming polymer and the sheath-forming material through the distribution plates to form the sheath/core bicomponent fibers.
Figure 41:
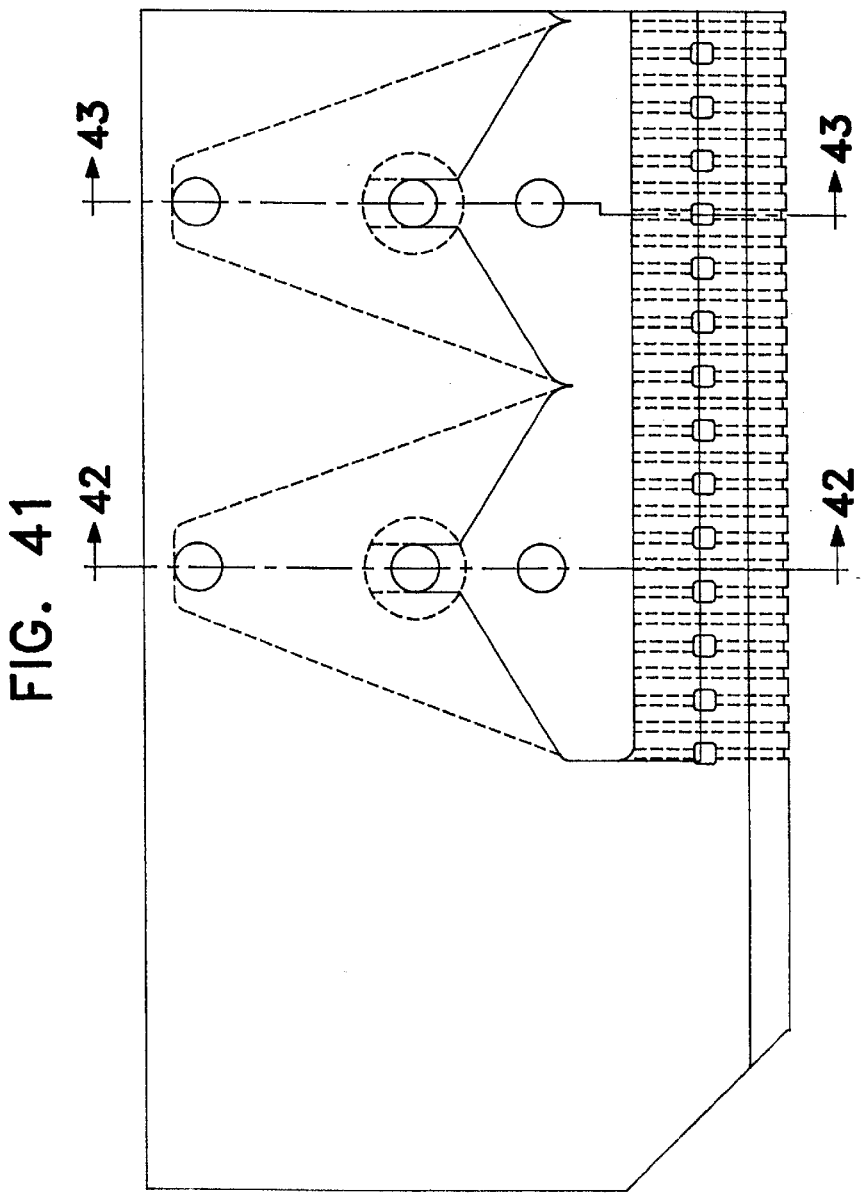
FIG. 41 is an assembled upstream plan view of the distribution plates illustrated in FIG. 39, with hidden parts shown in dotted lines for illustrative clarity.

The core-forming polymer then proceeds through four screen packs (not shown) into mating cutouts 702 in the downstream surface of left-hand nozzle 700, see FIG. 2, from which the core-forming polymer passes completely through the left-hand nozzle 700 riding up into a number of small grooves or distribution paths 704 on the upstream surface of the left-hand nozzle 700 which feed the core-forming polymer into larger cutouts 706 as seen in FIG. 1. From here, the core-forming polymer is fed into the distribution plate system.

As the core-forming polymer exits the cutouts 706 of the left-hand nozzle 700, it passes through distribution holes 602 in the secondary left distribution plate 600 and mating distribution holes 502 in the left distribution plate 500 filling up triangular cutouts 504 on the upstream surface of the left distribution plate.

At this point, the core-forming polymer literally travels around bosses 506 and 508 which surround first and second sheath-forming polymer distribution openings 510 and 512 to be discussed below and passes immediately into the inlet ends of each of the spinneret orifices 514, 516 as seen best in FIG. 24. The spinneret orifices 514, 516 are alternating spaced holes parallel to the plane of the left distribution plate 500, defined through the thickened lip portion 517 along the exit edge of the left distribution plate 500.

As discussed in more detail hereinafter, as the core-forming polymer passes into and through the spinneret openings 514, 516, it is enveloped by the first and second sheath-forming polymers, respectively, to extrude a uniform or homogeneous mixture of alternating bicomponent fibers which share the same core-forming polymer, and comprise different sheath-forming polymers.

Referring now the distribution path of the first sheath-forming polymer, after passing through the openings 106 in the mounting block 100, the first sheath-forming polymer collects in cutouts 114 on the downstream side of the mounting block 100. See FIG. 2. The first sheath-forming polymer then proceeds through four screen packs (not shown) into mating cutouts 202 on the upstream side of right-hand nozzle 200, passing through the right-hand nozzle 200 into distribution paths 204 which communicate with larger cutouts 206 on the downstream side of the right-hand nozzle 200. From here the first-sheath forming polymer is fed into the distribution plate system.

The first sheath-forming polymer exits the cutouts 206 in the right-hand nozzle 200, entering slots 302 of the secondary right distribution plate 300, filling up triangular cutouts 402 on the upstream side of the right distribution plate 400. From this point, the first sheath-forming polymer is divided into two separate distribution paths to allow the first sheath-forming polymer to envelop the core-forming polymer from both sides as these fiber-forming polymers pass through alternate spinneret openings 514 to provide a complete sheath covering over the core-forming polymer in the first sheath/core bicomponent fibers.

Half of the first sheath-forming polymer in the cutouts 402 enters distribution holes 404, passing through the right distribution plate 400. The other half of the first sheath-forming polymer passes around bosses 406 surrounding distribution openings 408 for the second sheath-forming polymer as discussed below. Half moon shaped spacers 409 are provided on either side of the distribution openings 404 to assist in withstanding pressure between the distribution plates, particularly in the areas of substantial cutouts such as the cutout 402, in the die assembly. This portion of the first sheath-forming polymer passes through alternating slots 410 formed on a scalloped thickened lip 412 on the edge of the right distribution plate 400 (see FIGS. 16 and 17) entering mating slots 518 in the left distribution plate 500 to envelop one side of the core-forming material passing into alternate spinneret openings 514.

The portion of the first sheath-forming material passing through distribution openings 404 mates with distribution openings 510, referred to above, on the upstream surface of the left distribution plate 500. This portion of the first sheath-forming polymer passes through the distribution openings 510 into short triangular cutouts 520 on the downstream side of the left distribution plate 500. At this point this portion of the first sheath-forming polymer enters alternating slots 522 on the scalloped side of the lip 517, enveloping the opposite side of the core-forming polymer.

With the core-forming polymer enveloped from both sides by the first sheath-forming polymer, the first sheath/core bicomponent fibers are extruded from the alternate spinneret opening 514 in the left distribution plate 500.

Dealing now with the distribution path for the second sheath-forming polymer, having exited a melt pump it is passed through external screen packs (not shown) and fed into the openings 110 in the mounting block 100, being directed therein to exit openings 116 on the downstream surface thereof See FIG. 2. The openings 116 mate with openings 208 which pass through the right-hand nozzle 200 into expanded cutouts 210 on the downstream side thereof See FIG. 2.

From cutouts 210 of the right-hand nozzle 200, the second sheath-forming polymer enters triangular cutout 304 on the upstream surface of the secondary right distribution plate 300. At this point, the second sheath-forming polymer is divided into two separate distribution paths to allow the second sheath-forming polymer to envelop the core-forming polymer from two sides in alternate spinneret openings to provide a complete sheath covering the core-forming polymer and to thereby extrude the second sheath/core bicomponent fibers through those spinneret openings.

Half of the second sheath-forming polymer passes through distribution openings 306 in the secondary right distribution plate 300, while the other half passes from the cutouts 304 directly into slots 308 juxtaposed to one edge of the secondary right distribution plate 300. Spacers 310 are again provided to maintain the proper spacing between the elements of the die assembly.

The half of the second sheath-forming polymer that goes through the slots 308 of the secondary right distribution plate 300 pass through mating slots 414 formed in the scalloped edge portion 412 on the upstream side of the right distribution plate 400 (see FIGS. 16 and 19) into mating slots 518 in the raised lip 517 of the left distribution plate 500 from which the second sheath-forming polymer envelops that side of the core-forming polymer.

The half of the second sheath-forming polymer that enters distribution hole 306 of the secondary right distribution plate 300 proceeds through mating hole 408 in the right distribution plate 400, mating hole 512 of the left distribution plate 500, and mating holes 604 of the secondary left distribution plate 600 to fill up the small triangular pocket 606 on the downstream side thereof. That portion of the second sheath-forming material then passes back through slots 608 in the secondary left distribution plate 600 which mate with slots 524 in the scalloped side of the lip 517 of the left distribution plate from which it envelops the opposite side of the core-forming polymer passing through alternate spinneret openings 516. In this manner, the second sheath-forming polymer envelops both side of the core-forming polymer in alternate spinneret openings 516 to extrude second sheath/core bicomponent fibers from every other spinneret opening.

With the foregoing explanation in mind, it will now be seen that the spinning device of FIGS. 1–33 is adapted to provide a homogeneous or uniform distribution of mixed fibers, every fiber having the same core-forming material, with every other fiber having a different sheath-forming material. The ability to form alternate sheath/core bicomponent fiber in this manner would not be possible without the presence of the right and left secondary distribution plates which enable the different sheath-forming polymers to be maintained in separate distribution paths and divided so that a portion of each sheath-forming polymer is delivered to one side of the core-forming material passing through alternate spinneret openings, and the remainder of each sheath-forming polymer is passed through the pack of distribution plates and returned to the opposite side of the core-forming polymer to completely envelop alternate core-forming polymer streams with the different sheath-forming polymers.

The secondary distribution plates, 300 and 500 allow the second sheath-forming polymer to pass through the system free of any contact with first sheath-forming polymer, the distribution paths needed for the second sheath-forming polymer to travel in this manner residing in the secondary distribution plates. When the first sheath-forming polymer enters the triangular cutouts 402 of the right distribution plate 400, the circular bosses 406 block the first sheath-forming polymer from mixing with the second sheath-forming polymer passing through the openings 408. The scalloped boss 412 serves the same purpose. As the first sheath-forming polymer proceeds down the triangular cutouts 402 to slot 410, the scalloped boss 412 prevents the first sheath-forming polymer from entering the slots 414 intended to receive the second sheath-forming polymer.

Likewise, the circular bosses 506 and 508 on the left distribution plate 500 prevent the core-forming polymer from mixing with either of the sheath-forming polymers, and vice-versa and the scalloped formations on the lip 517 of the left distribution plate 500 separates the sheath-forming polymers from each other.

The uniform distribution of these two dissimilar fibers in the web of fibers is enhanced by the use of a single line of spinneret orifices in the edge portion of one of the distribution plates, in this instance, the left distribution plate 500. If an array of spinneret openings in multiple planes is utilized, the ability to provide uniform distribution of fibers with different characteristics is complicated. This is particularly true in a melt blowing operation, as discussed below, wherein a fluid such as air under pressure is directed across the spinneret openings as the fibers emanate therefrom to attenuate the fibers while the polymer is still molten. With more than one stream of fibers, the melt blowing fluid tends to cause some of the fibers to flip over thereby reducing the homogeneity of the mixture of fibers in the resultant web.

The uniformity of the individual fibers produced by the spinning device of this embodiment of the instant invention is further enhanced by the formation of spinneret openings laterally through the raised lip 517 in the left distribution plate 500, rather than forming half of each spinneret opening by mating surfaces of juxtaposed distribution plates as in the prior art. With the construction of the spinneret openings disclosed herein, the fiber-forming surface is continuous and seamless, precluding any loss of fiber-forming polymer that may result from imperfect mating of the sealing surfaces forming the spinneret openings.

Of course, the shape of the spinneret openings can be chosen to accommodate the cross-section desired for the extruded fibers. While circular spinneret openings are commonly utilized, other non-round cross-sections may be provided for special applications. Multi-lobal fibers, i.e., X-shaped, Y-shaped, or other such cross-sections (not shown) are possible. With the instant inventive concepts, alternate spinneret openings can have different configurations to provide a uniform mixture of fibers of different cross-sections.

Referring now to FIGS. 34–38, the distribution plates of a simplified form of the spinning apparatus described hereinabove is illustrated. In this embodiment, only two independent sources of polymer materials are provided, the alternate fibers in the homogeneous web of fibers being formed of the polymer from only one of the sources. It is to be understood that, as described with respect to the embodiment of FIGS. 1–33, the embodiment of FIGS. 34–38 would include a mounting block such as the mounting block 100, a right-hand nozzle, such as the right-hand nozzle 200, a left-hand nozzle, such as the left-handle nozzle 700, and a clamp block, such as the clamp block 800 shown in the earlier Figures, although these elements have not been included in FIGS. 34–38 for illustrative convenience. In this instance, however, only two, distribution plates are necessary, identified in FIGS. 34–38 as right distribution plate 60 and left distribution plate 70, the secondary right and left distribution plates being unnecessary since only two polymers are being processed in this system.

The first polymer enters the distribution plate system on the upstream side of the right distribution plate 60 filling up the triangular cutouts 61 defined therein. Half moon spacers 62 and circular spacers 63 are provided in the triangular cutouts 61 to maintain the proper distance between the right distribution plate 60 and the right-hand nozzle (not shown in these Figures). At this point, the first polymer is divided into two portions, one portion passing through the distribution holes 64, the remaining portion passing into the slots 65.

The portion of the first polymer that goes into the distribution holes 64 passes through mating distribution holes 71 in the left distribution plate 70. The distribution holes 71 are surrounded by bosses 72 in triangular cutouts 75 formed in the upstream surface of the left distribution plate 70. The bosses 72 in concert with spacers 74 protect the left distribution plate 70 from distortion.

This portion of the first polymer enters triangular cutouts 75, also provided with spacers 74 on the downstream surface of the left distribution plate 70. This portion of the first polymer then passes directly into slots 77 which communicate with one side 78 of enlarged portions at the base of alternating spinneret openings 79 in the left distribution 70.

The portion of the first polymer passing through the slots 65 in the right distribution plate 60 is received directly on the opposite sides 66 of the enlarged portions of the spinneret openings 67, the two portions of the first polymer being thereby joined to extrude through the alternating spinneret openings formed by the grooves 67, 79 to form spaced monocomponent fibers of the first polymer.

The second polymer is received from the right-hand nozzle as in the earlier embodiment, passing uninterrupted through right and left distribution plates 60, 70 to the clamp block which returns the second polymer through the left-hand nozzle into distribution openings 78 in the downstream surface of the left distribution plate 70. As the second polymer passes through the distribution openings 78 it is received in the triangular cutouts 73 on the upstream face of the left distribution plate 70. A portion of the second polymer in the cutouts 73 flows down about bosses 72 and spacers 74 to grooves 76 forming portions of the spinneret openings in the left distribution plate 70. The remainder of the second polymer in the cutouts 73 on the upstream surface of the left distribution plate 70 flows into the triangular cutouts 68 on the downstream side of the right distribution plate 60 to flow therefrom through the opposite portions 69 of the alternate spinneret openings for the second polymer material.

Thus, in this embodiment, molten polymer from two independent sources are fed through the die assembly, the two distribution plates extruding polymer from each source through alternate spinneret openings, thereby forming a homogeneous mixture of monocomponent fibers, fibers of one polymer being side-by-side with fibers of the other polymer in the web.

Referring now to FIGS. 39–43, the distribution plates of yet another embodiment of spinning device according to the instant inventive concepts are illustrated, this embodiment spinning a web of fibers, wherein selected fibers comprise sheath/core bicomponent fibers, which alternate with monocomponent fibers formed of the core-forming polymer. Again, since only two fiber-forming polymers are processed in this system, only two distribution plates are necessary, the secondary right and left distribution plates of the embodiment of FIGS. 1–33 being eliminated.

It will be understood that the sheath-forming polymer and the core-forming polymer of the bicomponent fibers to be extruded from the distribution plates of this embodiment are received from independent polymer sources, passing through a mounting block such as the mounting block 100, a right-hand nozzle, such as the right-hand nozzle 200, the distribution plate system, which in this instance comprises the right distribution plate 80 and the left distribution plate 90, with a left-hand nozzle such as the left-hand nozzle 700 and a clamp block such as the clamp block 800 completing the die assembly, but not being shown in FIGS. 39–43.

The polymer forming both the monocomponent fibers in this system and the core of the bicomponent fibers passes straight through all the die plates in one interrupted stream and enters the clamp block where it is reversed and passed back through the left-hand nozzle to be received in openings 91 on the downstream face of the left distribution plate 90, passing therethrough into the triangular cutouts 92 on the upstream face thereof. A portion of the core-forming polymer passes directly from the cutouts 92 into each of the alternating grooves 93, 94 forming half of the spinneret openings for the monocomponent and bicomponent fibers, respectively.

The remainder of the core-forming polymer from the cutouts 93 enters the mating triangular cutouts 81 on the downstream surface of the right distribution plate 80 to pass into the inlet portions of the grooves 82, 83, forming the opposite portions of the spinneret openings.

The material received in the mating grooves 82, 93 is extruded from alternate spinneret openings as monocomponent fibers formed of the core-forming polymer. The material received in the mating grooves 83, 94 form the central core of the sheath/core bicomponent fibers to be extruded from alternate spinneret openings as discussed below.

The sheath-forming polymer is received from the right-hand nozzle and fills up the triangular cutouts 84 in the upstream face of the right distribution plate 80 where it is divided into two portions. One portion passes directly through the distribution openings 85 in the right distribution plate 80 and the aligned opening 95 in the left distribution plate 90 to the triangular cutouts 96 in the downstream surface thereof. That portion of the sheath-forming polymer passes through slots 97 into enlarged openings 98 to encompass one side of the core-forming polymer as it is extruded from the spinneret openings partially defined by the grooves 94.

The other portion of the sheath-forming polymer passes from the triangular cutouts 84 through the slots 87 to be received in the enlarged portions 88 of the grooves 83 in the right distribution plate 80 to encompass the other side of the core-forming material, thereby extruding sheath/core bicomponent fibers from the alternating spinneret openings.

Appropriate bosses and spacers are provided in each of the larger cutout areas to insure that the individual distribution plates are not distorted by the pressure of the molten polymer in these thinned out portions of the distribution plates.

As will now be evident, the embodiment of FIGS. 39–43 enables the production of a homogeneous mixture of bicomponent and monocomponent fibers wherein the monocomponent fibers are formed of the core-forming polymer of the bicomponent fibers.

The web of homogeneously or uniformly distributed fibers extruded from any of the embodiments of the spinning device of the instant invention may be subsequently treated by conventional techniques to produce products of unique characteristics. For example, with an embodiment as simple as the mixed monocomponent system of FIGS. 34–38, the same or different polymers can be fed into a die assembly 900 under different pressures or at different speeds so that the speed of extrusion of the polymer material through alternate spinneret openings is different. If a web of fibers 902 formed in this fashion is taken up by a single pair of nip rolls 904 as shown in FIG. 44, alternating fibers will be attenuated differently. If the speed of rotation of the nip rolls is the same as the speed of extrusion of one of the polymers, but faster than the speed of extrusion of the other polymer, the fibers formed from the one polymer will not be attenuated at all, and the fibers formed from the other polymer will be attenuated, resulting in a mixed web of fibers of the same or different polymer, but of different denier. This uniformly distributed type of mixed fibers can then be subsequently processed in any conventional way, providing products which have relatively thicker fibers, perhaps contributing strength to the product, admixed with relatively finer fibers, perhaps for increased filtration efficiency.

Another application of a web of mixed fibers produced according to the various embodiments of the instant inventive concepts discussed above, is the alternate extrusion of fibers containing a bondable surface with fibers which are not readily bondable by commercial processing equipment. In this situation, materials that are otherwise difficult to bond, but have chemical or physical characteristics that are important to an end product, can be effectively bonded in an economical manner.

For example, with reference to FIGS. 45 and 46 one form of a process line for producing continuous, elongated, porous rods is schematically illustrated at 910 wherein a web of such mixed fibers 912 may be bonded to each other at spaced points of contact to produce a tortuous path for the passage of a fluid, perhaps to filter undesirable constituents therefrom as in the production of tobacco smoke filters. Depending upon the particular polymers exposed at the surface of the adjacent fibers in the web, the bonded porous elements resulting therefrom may be effective as coalescing filters, medical filters, heat and moisture exchangers, wick members, absorptive elements, and the like, any of the general applications having been mentioned hereinabove and many others.

While the processing line 910 illustrated in FIGS. 45 and 46 is only exemplary, a web of mixed fibers produced by the spinning device of this invention may be passed through a high velocity air stream such as provided through an air plate shown schematically at 914, to attenuate and solidify the fibers, enabling the production of ultra-fine fibers, on the order of ten microns or less. Such treatment produces a randomly dispersed and tangled web 916 of the fibers, which is in a form suitable for immediate processing without subsequent attenuation or crimp-inducing processing.

If desired, a layer of particulate additive, such as granulated activated charcoal, may be deposited on the web or roving 916 as shown schematically at 918. Alternatively, a liquid additive such as a flavorent or the like may be sprayed onto the tow 916 at 918. A screen-covered vacuum collection drum (not shown), or a similar device, may be used to separate the fibrous web or roving 906 from entrained air to facilitate further processing.

The remainder of the processing line 910 as seen in FIG. 45 is conventional and is shown and described in my aforementioned '430 patent, and other of my prior art patents, although modifications may be required to individual elements thereof in order to facilitate heat-bonding of particular mixtures of fibers.

The illustrated heat-bonding techniques show the web or roving of the mixed fibers 916 produced from the melt blowing techniques to be passed through a conventional air jet at 920, bloomed at seen at 922 and gathered into a rod shape in a heated air or steam die 924 where a bondable material in at least some of the fibers of the web is activated to render the same adhesive. The resultant material may be cooled by air or the like in the die 926 to produce a relatively stable and self-sustaining rod-like fiber structure 928.

Depending upon the ultimate use of the rod 928, it may be wrapped with paper or the like 930 in a conventional manner to produce a continuously wrapped fiber rod 932. The continuously produced fiber rod 932, whether wrapped or not, may be passed through a standard cutter head 934, at which point it may be cut into preselected lengths and deposited on a conveyor belt 936 for subsequent processing, or for incorporation into other equipment.

Obviously, depending upon the particular fibers in the web and their individual chemical and physical characteristics, the post-extrusion processing of the web of fibers can be modified as necessary to produce the desired product.

Regardless of the selection of polymer components, the advantages of producing a homogeneous and uniformly distributed mixture of fibers of differing characteristics, even including bicomponent fibers having different sheath-forming polymeric coatings, is readily recognized. Significant cost reductions can result from the use of relatively inexpensive core materials, with limited amounts of a more expensive sheath-forming polymer, or even two different sheath-forming polymers, to provide particular attributes to the final products.

In each of the embodiment disclosed herein, a web of fibers is shown as having alternately extruded fibers of differing characteristics. While such an arrangement is desirable for most applications, with relatively minor modifications, one type of fiber can be extruded through every third spinning orifice, every fourth spinning orifice, etc., thereby providing a web of homogeneously mixed fibers, wherein the different fibers are not necessarily present in a 50/50 ratio.

Reference will now be made to various applications of the improved mixed fiber technology described herein above. One particular such use is in the provision of high filtration products for electrical dust collection devices and other such demanding environments, including baghouse filters used in power plants to filter flue gases. It has been found that filters comprising a uniquely homogeneous mixture of homopolymers or copolymers of fluorocarbon polymers or chlorinated fluorocarbon polymers with nylon fibers produces significantly improved filtration efficiently as compared with filters formed from either polymer alone.

The fluorocarbon and chlorinated fluorocarbon polymers and their copolymers naturally carry a negative charge and nylon naturally carriers a positive charge. Hydrophilic nylon, discussed below in detail with respect to the HME concepts of this invention, is particularly desirable because of its high hydrophilic properties. However, other forms of nylon polymer are also effective in this application.

The nature of the fluorocarbon or chlorinated fluorocarbon polymers and copolymers used is generally dictated by their spinning properties. HALAR® ECTFE fluoropolymer, commercially available from Ausimont USA, Inc., a subsidiary of Montedison, is the preferred material for this use. Although other fluorocarbon polymers or chlorinated fluorocarbon polymers or copolymers of such polymers may be used for several applications of the instant inventive concepts, for simplification the following discussion will refer to HALAR® as exemplary of any such materials.

A homogeneous mixture of fibers having surfaces of these polymers provides unexpectedly improved filtration properties, even with reduced weight of materials. Since HALAR® is quite expensive, bicomponent fibers comprising on the order of 10–20% by weight of a HALAR® sheath over a nylon core in a homogeneous mix with monocomponent fibers formed of nylon, significantly reduces the cost. The apparatus illustrated in FIGS. 39–43 may be advantageously used to produce such a mixture of fibers. Although a 50/50 mixture of these fibers is particularly adapted for many applications, the nylon fibers, which act as a bonding agent, may be present at levels of 40% or even less.

Alternatively, using the apparatus of FIGS. 1–33, a homogeneous mix of bicomponent fibers having alternating sheaths of HALAR® and nylon over a relatively inexpensive common core material such as polypropylene, can be produced to even further reduce the cost of the ultimate product.

Preferably, in the formation of filtering materials from a homogenous mixture of HALAR® and nylon containing fibers, the web of fibers would be melt-blown and processed as shown in FIGS. 45 and 46 to produce very fine fibers, on the order of 10 microns or less.

The filter itself could take various forms depending upon its particular application. A simple calendered non-woven sheet is appropriate for some applications such as in assays from medical tests. Alternatively, the sheet material can be pleated to increase the surface area, using standard techniques, some of which are shown in my prior patents.

For other applications, the mixed fibers can be formed into a continuous porous element according to the techniques shown in FIGS. 45 and 46 to produce plugs of filter material. Another form that the filter may take, would be a hollow tube, formed from the homogeneous web of mixed fibers according to any conventional manufacturing technique usually incorporating a central mandrel in the forming zone to produce an annulus.

In Table 1, below, a comparison of 27 millimeter plugs formed of a 50/50 HALAR®/nylon mix of fibers, with plugs formed of 100% nylon fibers and plugs formed of 100% HALAR® fibers is seen.

TABLE 1

| | 27 mm Plug | | |
|---|---|---|---|
| SAMPLE | WT. | TIP PD | RETENTION (%) |
| 100% Nylon | 11.2 g/m | 4.4 | 72.64 |
| 100% Halar ® | 8.4 g/m | 4.7 | 69.38 |
| Halar ®/Nylon (50/50) | 5.3 g/m | 4.6 | 80.02 |

From the above Table, it will be recognized that, with similar pressure drops, the retention of a plug formed according to the instant inventive concepts from a homogeneous mixture of fibers of HALAR® and nylon, has a significantly higher filtration efficiency (retention percent) than corresponding plugs formed of 100% nylon and 100% HALAR®, notwithstanding the lower weight of materials in the plugs of this invention.

Table 2 compares flat surface elements formed from a mixed fiber HALAR®/nylon web according to this invention, cut as Cambridge filtration pads, with elements formed of 100% nylon and 100% HALAR®.

TABLE 2

| Flat Surface Cut as Cambridge Filtrona Pad | | | |
|---|---|---|---|
| SAMPLE | WT. | PAD PD | RETENTION (%) |
| 100% Nylon | 0.6403 | 0.1 | 47 |
| 100% Halar ® | 0.621 | 0.1 | 48.94 |
| Halar ®/Nylon (50/50) | 0.6329 | 0.1 | 52.05 |

Again, improved filtration efficiency is seen.

Another application for the improved mixed fiber technology of this invention is the production of a coalescent-type filters such as those used to separate water from aviation fuel. Hydrophobic fibers are needed for this type of filter to allow the water to be held and not spread along the fiber. Currently, such products are made of silicon-coated fiberglass.

Utilizing the low surface tension of HALAR®, and the ability to create small fibers using melt-blown techniques, which help to collect small droplets of water, it has been found that the HALAR® fibers can be bonded into a highly efficient coalescent filter by spinning a mixed fibrous web comprising the HALAR® fibers and a bonding fiber. Although other bonding fibers can be used, such as polypropylene or polyethylene, it is preferred to use polyester fibers, such as polyethylene terephthalate, because such material is very inert, and in its amorphous state provides excellent bonding for the HALAR® fibers in the presence of steam. Moreover, polyethylene terephthalate does not stick to the equipment, a problem common with polypropylene and/or polyethylene.

As discussed above with respect to the high filtration products, the HALAR® fibers can be formed as bicomponent fibers, either with a core of polyethylene terephthalate extruded side-by-side with polyethylene terephthalate monocomponent fibers according to the techniques of FIGS. 39–43, or the HALAR® and polyethylene terephthalate polymers may each be extruded as bicomponent fibers with a core of polypropylene or the like using the apparatus of FIGS. 1–33 to reduce the cost and improve the strength of the ultimate product.

As noted, for coalescent applications, the fibers are preferably very fine, certainly less than about 10 microns. The high surface area of these hydrophobic fibers causes the water to bead up and thereby facilitates separation of water from a mixture of water with a petroleum product such as aviation fuel.

Coalescent-type filters according to this invention can be formed in any of a variety of configurations, e.g., laid down webs, preferably pleated pads, plugs, and, for many applications, tubes, using conventional technology.

A third application of the instant inventive concepts is the production of a homogeneous mixture of nylon and polyethylene terephthalate fibers to create a wicking product for use as a reservoir in the transfer of ink in marking and writing instruments, or for medical wicks or other products designed to hold and transfer liquids, many of which are discussed in detail my prior '082 patent. Polyethylene terephthalate is preferred over other bonding fibers for the same reasons discussed above with respect to its selection in the production of coalescent filters. Moreover, polyethylene terephthalate has a higher surface energy than the polyolefins, which allows it to wick more liquids.

The use of very fine fibers, on the order of 3–7 microns enhances the absorption effectiveness as would be expected.

By reference to Table 3, an ink reservoir product currently in use in marking and writing instruments and commercially available from the assignee of the instant application under the trademark TRANSORB®, is compared with melt-blown mixed fiber products according to this invention comprising polyethylene terephthalate and nylon.

TABLE 3

| SAMPLE | WT. | LENGTH | DIAMETER | ABS ($H_2O$) % ABSORPTION | ABS 48 DYNE % ABSORPTION |
|---|---|---|---|---|---|
| XPE-PET w/surfactant | 0.7776 | 88 | 6.71 | 74.58 | 74.58 |

TABLE 3-continued

| SAMPLE | WT. | LENGTH | DIAMETER | ABS (H₂O) % ABSORPTION | ABS 48 DYNE % ABSORPTION |
|---|---|---|---|---|---|
| PET 4449/Nylon SCFX6 | 0.7067 | 88 | 6.82 | 86.84 | 82.89 |
| PET 4449/Nylon SCFX6 | 0.8072 | 88 | 7.91 | 86.78 | 86.30 |

The above Table shows the surprising increase in absorption produced from plugs of the mixed polyethylene terephthalate/nylon products, as compared to the commercially available TRANSORB® product.

The polyethylene terephthalate/nylon mixed fiber products of this invention are particularly useful in writing instruments due to the hydroscopic nature of the nylon. Such products show an improvement in absorption over standard olefin and polyethylene terephthalate samples, even those including a surfactant. See Table 4.

TABLE 4

| SAMPLE | WT. | LENGTH | DIAMETER | ABS (H₂O) % ABSORPTION | ABS (ALCOHOL) % ABSORPTION |
|---|---|---|---|---|---|
| Olefin w/surfactant | 2.0110 | 100 | 12.30 | 69.19 | 73.74 |
| PET w/surfactant | 1.3020 | 100 | 11.86 | 59.63 | 65.61 |
| Nylon/PET 60/40 w/o surfactant | 1.2446 | 100 | 12.41 | 84.05 | 77.24 |
| Nylon/PET 60/40 w/o surfactant | 0.6690 | 100 | 7.63 | 92.56 | 87.75 |

A variation on the foregoing application is the production of an insoluble resin that is hydrophilic, particularly for writing and medical products where nylon may interfere with the assay or chemistry. In such instances, the products formed from a uniformly mixed web of polyvinyl alcohol and polyethylene terephthalate fibers can be produced, the polyethylene terephthalate being desirable for its unique bonding capabilities as well as its inertness and high temperature resistance. Polyvinyl alcohol is advantageous because it is one of the few hydroscopic fibers which may be soluble at different temperatures. Polyvinyl alcohol fibers mixed with polyethylene fibers could be used for the production of less expensive filters wherein the required properties are not as demanding.

From the foregoing, it will be recognized that the mixed fiber technology of the instant invention enables the production of diverse products with unexpectedly improved functional properties, resulting at least in significant part from the exceptional uniformity and homogeneity of the distribution of the different fibers in the web. Moreover, the use of the technology of this invention enables the production of such products in a highly efficient, commercially desirable, manner, overcoming many of the disadvantages both in the prior art products, as well as in the methods and apparatus for making such products.

Finally, a unique application of the instant inventive concepts is in the production of a novel heat and moisture exchanger (HME) which may be made using the mixed fiber technology of this invention to even further improve the functional aspects of the product and enable its production in a less expensive, more effective manner. In this respect, reference is made initially to FIGS. 47 and 48. In FIG. 47 an intubated patient 950 is schematically illustrated, with an HME 960 according to the instant inventive concepts being interposed in an artificial airway 970 which communicates the patient's respiratory tract with the atmosphere as schematically shown by arrows 980 and/or with a source of an incoming gas, such as oxygen or an anesthetic, as schematically shown by arrows 990.

The artificial airway 970 can communicate through the HME directly between the patient's respiratory tract and the atmosphere, as in a tracheotomy. Alternatively, the artificial airway 970 may communicate through the HME with a standard commercially available short- or long-term mechanical ventilator (not shown), or a source of a dry gas such as an anesthetic in a medical theater, or, possibly, oxygen as may be found in an intensive care unit or a patient's hospital room. If necessary or desirable, a "Y" connector 972 as shown in dotted lines may connect the HME with the artificial airway 970 via a valve of any conventional nature, shown schematically at 974, to permit the breathing circuit to cycle between inspiration and exhalation in a well known manner.

The HME 960 can take any conventional form, but regardless of design, will include a heat and moisture exchanger element shown in dotted lines in FIG. 47 at 962 within a housing 964. The element 962 according to the instant inventive concepts is a gas-permeable media adapted to be warmed and to trap moisture from a patient's breath during exhalation, and to be cooled and to release the trapped moisture for return to the patient during inspiration, formed, at least in part, of a hydrophilic nylon polymer in sufficient quantity to effectively conserve the humidity and body heat of the patient's respiratory tract.

Hydrophilic nylon polymers are known and it is believed that any of these materials may be used in the production of an HME according to the instant invention concepts. Such materials have been used heretofore for various applications, primarily in the production of apparel. Other uses include face masks, prosthesis liners to protect sensitive skin from abrasion discomfort due to the presence of body moisture, incontinence garments, and other personal protection devices.

A particularly desirable hydrophilic nylon is available commercially under the trademark Hydrofil® from Allied Fibers, and is a block copolymer of nylon 6 and polyethylene oxide diamine (PEOD). The ratio by molecular weight is approximately 85% nylon 6 and 15% PEOD. Hydrofil® nylon resin is designed for fiber extrusion but it has been successfully melt-blown and spun-bonded for use in the production of non-wovens for the aforementioned and other such fields. Fibers produced of this polymer are said to have a higher elongation and a lower tenacity than traditional nylon, with a melting point only about 1–2 degrees lower than nylon 6 and a softening point about 40° lower. This hydrophilic polymer is said to yields fibers that are more amorphous, much softer and much more absorbent than nylon.

The gas-permeable element 962 may be formed in a variety of ways. It could simply be a hydrophilic nylon polymeric shaped member provided with passageways communicating the upstream and downstream ends so that a gas, whether it be the patient's inhaled or exhaled breath, or an extraneous gas such as oxygen or an anesthetic, can readily pass through the element, as necessary.

Preferably, however, the gas-permeable element 962 of the instant invention is a fibrous media comprising a multiplicity of fibers having at least a surface of the hydrophilic nylon polymer. Of course, the fibers can be entirely formed of a hydrophilic nylon polymer and bonded at their points of contact to form interconnecting passages from one end to the other. For example, a multiplicity of hydrophilic nylon polymeric fibers can be extruded in any conventional manner from a spinneret onto a continuously moving surface to form an entangled fibrous mass which may be calendered to bond the fibers to each other and thereby form a porous sheet or pad removably retained in the housing 964 of the HME 960 for replacement as needed.

Alternatively, and preferably, a bonding agent can be incorporated in any conventional manner into a mass of fibers comprising a hydrophilic nylon polymer to bond the hydrophilic nylon fibers to each other at their points of contact into a three-dimensional porous element defining a tortuous path for passage of a gas therethrough. The bonding agent is also preferably provided as a multiplicity of fibers comprising at least a surface of a polymer having a lower melting point than the hydrophilic nylon, such as a polyester, for example, polyethylene terephthalate.

Such mixed fibers can be processed in any conventional manner to form the gas-permeable element 962. For example, the fibers can be gathered into a rod-like shape and passed through sequential steam-treating and cooling zones to form a continuous three-dimensional porous element, portions 962 of which can be incorporated as a plug in the HME housing 964 to provide a tortuous path for passage of a gas therethrough.

In order to minimize the cost of the relatively expensive hydrophilic nylon polymer, bicomponent fibers can be formed in any conventional manner, comprising a sheath of the hydrophilic nylon polymer and a core of a less expensive thermoplastic polymer such as, for example, polypropylene. Such bicomponent fibers can then be bonded as discussed previously to produce the gas-permeable element for use as an HME according to the instant inventive concepts. Such a core-forming polymer is not only less expensive, but provides the fibrous media with increased strength to lengthen the effective life of the HME.

Finally, and most preferably, both the hydrophilic nylon polymer fibers and the bonding agent fibers can be formed as bicomponent fibers, preferably provided with a common core-forming thermoplastic polymer, such as polypropylene. In this fashion, reduced costs and increased strength will be provided to the HME by both the hydrophilic nylon fibers and the bonding agent fibers.

The preferred production of a web of fibers comprising a homogeneous mixture of fibers formed from different polymeric materials for the production of an HME according to this invention is described above with particular reference to FIGS. 1–46. Utilizing the techniques disclosed in FIGS. 34 to 38, a uniformly distributed mixture of monocomponent fibers, some of which are formed entirely of hydrophilic nylon and others of which are formed entirely of a bonding agent polymer, can be readily extruded, melt-blown and subsequently processed into a continuous rod-like porous element as shown in FIGS. 45 and 46. Alternately, as disclosed in FIGS. 39 to 43, monocomponent bonding agent fibers can be extruded side-by-side with bicomponent fibers having a core of the polymer from which the monocomponent fibers are made, e.g., a polyester, and a sheath of the hydrophilic nylon polymer. Finally, utilizing the techniques of FIGS. 1 to 33, a uniform web of mixed bicomponent fibers, some of which have a sheath of a hydrophilic nylon polymer, and others of which have a sheath of a bonding agent polymer, such as a polyethylene terephthalate, with all of the bicomponent fibers having a core of a thermoplastic material such as polypropylene, may be extruded and formed int a porous rod-like element in a simple and inexpensive manner.

Thus, while the HME media of this invention may be formed in a variety of ways, the preferred construction comprises a gas-permeable element formed of a homogeneous mixture of bicomponent fibers having respective sheaths of hydrophilic nylon and polyester produced according to the improved mixed fiber technology disclosed herein and bonded at their points of contact to define a tortuous path of a passage of a gas therethrough.

The fibers utilized in the preparation of the HME according to the instant invention are preferably very fine in nature, having a diameter, on average, of ten microns or less. Such fibers, whether monocomponent or bicomponent fibers, or mixtures of monocomponent and bicomponent fibers, or mixtures of different bicomponent fibers, can be readily produced utilizing conventional melt-blowing techniques. The advantages of HMEs formed from such fine fibers is two-fold. First, the increased surface area afforded by the fibers provides more effective heat and moisture exchange properties. Moreover, the use of fine fibers of this nature also provides increased surface area and reduced interstitial spaces for filtering undesirable contaminants such as bacteria or viruses or other particulates from a gas passing therethrough.

With respect to the concomitant use of the HMEs of this invention as high efficiency particulate air (HEPA) filters, there are at least three known physical mechanisms by which particles of a gas may be captured by a filter media. First, and particularly for the larger particles, direct interception of the particles wherein they are physically removed on the upstream surface of the filter medium because they are too large to pass through the interstitial pores, is most significant. However, for smaller particles, inertial impaction, wherein the particles collide with the filter medium because of their inertia to changes in the direction of gas flow within the filter media, may be more significant. Finally, very small particles may be captured by diffusional interception wherein they undergo considerable Brownian motion, increasing the probability of efficient capture of such particles by the filter medium. For all practical purposes, it is believed that each of these mechanisms may be at work in the use of a hydrophilic nylon HME in an artificial airway according to the instant inventive concepts.

Although certain of the advantageous properties of hydrophilic nylon have been recognized for unrelated applications, the effectiveness of such materials in increasing the effectiveness of an HME, without the need for extraneous chemicals to enhance its hygroscopicity, is surprising. Moreover, the improved functional effectiveness of an HME formed from the unique homogeneous mixture of simultaneously extruded hydrophilic nylon and bonding agent fibers according to the mixed fiber technology of this application is even more unexpected. Additionally, as has been noted above, the ability to minimize the quantity of both the hydrophilic nylon polymer and the bonding agent polymer in the mixed fibrous web, significantly reduces the costs of the HME media while strengthening the same to withstand extended use, enabling an HME according to this invention to be manufactured inexpensively, and yet be readily disposed of and replaced between uses in a cost-efficient system. Finally, the ability of a melt-blown hydrophilic nylon HME to effectively function as a HEPA filter in an artificial airway of a medical device, enhances the advantages afforded by the instant inventive concepts.

With reference now to FIGS. 48a–48c, the use of an HME according to this invention is schematically illustrated. A plug of hydrophilic nylon-containing HME media is designated generally by the reference numeral 962 in each of these Figures. As the patient breathes out, illustrated by the arrows 980 in FIG. 48a, the media 962 captures the warmth and moisture from the patient's exhaled breath. When the patient breaths in as shown by the arrows 990 in FIG. 48b, condensate on the media 962 is evaporated and moisture is released so that the incoming gas is warmed and humidified as it is returned to the patient. FIG. 48c illustrates a repetition of the process of FIG. 48a the next time the patient exhales, the heat and moisture exchange sequentially and continuously taking place thereafter as gas passes to and through the media 962 in one direction and then the other.

It is to be understood that the various preferred embodiments of the instant inventive concepts discussed above are not independent of each other. For example, mixed fibers of different denier can be formed of the same polymer according to this invention, or of different polymers. Additionally, mixed fibers of different denier can be formed of both monocomponent and bicomponent fibers, or of different bicomponent fibers. Any of the products described above as formed of a homogeneous mixture of fibers of two polymers, made, for example, by the apparatus of FIGS. 34–38, can be modified to utilize a mixture of monocomponent fibers of one polymer with bicomponent fibers comprising a sheath of the second polymer and a core of the monocomponent fiber by utilizing equipment as shown in FIGS. 39–43. Finally, such products can be formed of sheaths of the two primary polymers with a core of a common third polymer with apparatus such as shown in FIGS. 1–33. Other obvious combinations of the various features of the instant inventive concepts will be readily apparent to those skilled in the art.

Having described the invention, many modifications thereto will become apparent to those skilled in the art to which it pertains without deviation from the spirit of the invention as defined by the scope of the appended claims.

What is claimed is:

1. For use in an artificial airway of a breathing circuit, a heat and moisture exchanger including a gas-permeable element, the improvement which comprises said element being formed, at least in part, of a hydrophilic nylon polymer in sufficient quantity to be warmed and to trap moisture from a patient's breath during exhalation, and be cooled and release the trapped moisture for return to the patient during inspiration to thereby effectively conserve the humidity and body heat of the patient's respiratory tract, said element being constructed to create a pressure drop sufficiently low to minimize effort during normal breathing of the patient or mechanical ventilation.

2. The heat and moisture exchanger of claim 1 wherein said hydrophilic nylon polymer is a block copolymer of nylon 6 and polyethylene oxide diamine.

3. The heat and moisture exchanger of claim 1 wherein said element is a fibrous media comprising fibers having at least a surface of said hydrophilic nylon polymer.

4. The heat and moisture exchanger of claim 3 wherein said fibers, on average, have a diameter of about 10 microns or less.

5. The heat and moisture exchanger of claim 4 wherein said fibrous media further functions as a filter media for particulate contaminants in gases passing through the breathing circuit.

6. The heat and moisture exchanger of claim 3 wherein said fibrous media further comprises a bonding agent, the hydrophilic nylon fibers being bonded at their points of contact by said bonding agent into a three-dimensional porous element defining a tortuous path for passage of a gas therethrough.

7. The heat and moisture exchanger of claim 6 wherein said bonding agent includes fibers comprising a thermoplastic polymer having a lower melting point than the melting point of the hydrophilic nylon polymer.

8. The heat and moisture exchanger of claim 7 wherein said thermoplastic polymer of said bonding agent fibers is a polyester.

9. The heat and moisture exchanger of claim 8 wherein said polyester is polyethylene terephthalate.

10. The heat and moisture exchanger of claim 3 wherein the hydrophilic nylon fibers are bicomponent fibers comprising a sheath of said hydrophilic nylon polymer and a core of a different polymer.

11. The heat and moisture exchanger of claim 10 wherein the core-forming polymer comprises polypropylene.

12. The heat and moisture exchanger of claim 10 wherein said fibrous media further comprises a bonding agent, said bicomponent fibers being bonded at their points of contact by said bonding agent into a three-dimensional porous element defining a tortuous path for passage of a gas therethrough.

13. The heat and moisture exchanger of claim 12 wherein said bonding agent includes fibers comprising a thermoplastic polymer having a lower melting point than the melting point of the hydrophilic nylon polymer.

14. The heat and moisture exchanger of claim 13 wherein said thermoplastic polymer of said bonding agent fibers is a polyester.

15. The heat and moisture exchanger of claim 14 wherein said polyester is polyethylene terephthalate.

16. The heat and moisture exchanger of claim 13 wherein said bonding agent fibers are bicomponent fibers comprising a sheath of said thermoplastic polymer and a core of the same polymer as the core of the hydrophilic nylon bicomponent fibers.

17. In combination, an endotracheal tube defining an airway for communicating a patient's respiratory tract with a source of ambient air, and a heat and moisture exchanger according to claim 1 interposed in said airway.

18. In combination, a breathing circuit including an airway for communicating a patient's respiratory tract with a mechanical ventilator, and a heat and moisture exchanger according to claim 1 interposed in said airway.

19. In combination, a breathing circuit comprising a source of oxygen, an airway for connecting said oxygen source to a patient's respiratory tract, and a heat and moisture exchanger according to claim 1 interposed in said airway.

20. In combination, a breathing circuit comprising a source of an anesthetic, an airway for connecting said anesthetic source to a patient's respiratory tract, and a heat and moisture exchanger according to claim 1 interposed in said airway.

21. In a method of conserving humidity and body heat of a patient's respiratory tract during treatment of the patient requiring connection of the patient to an extracorporeal source of gas through an airway, the improvement comprising interposing in the airway a heat and moisture exchanger including a gas-permeable element formed, at least in part, of a hydrophilic nylon polymer in sufficient quantity to be warmed and trap moisture from the patient's breath during exhalation, and to be cooled and release the trapped moisture for return to the patient during inspiration, said element creating a pressure drop sufficiently low to minimize effort during normal breathing of the patient or mechanical ventilation.

22. The method of claim 21 wherein said hydrophilic nylon polymer is a block copolymer of nylon 6 and polyethylene oxide diamine.

23. The method of claim 21 wherein said element is a fibrous media comprising fibers having at least a surface of said hydrophilic nylon polymer.

24. The method of claim 23 wherein said fibers, on average, have a diameter of about 10 microns or less.

25. The method claim 24 wherein said fibrous media defines a tortuous path for passage of the gas therethrough and thereby captures particulate contaminants contained in the gas.

26. The method of claim 23 wherein said fibrous media further comprises a bonding agent, the hydrophilic nylon fibers being bonded at their points of contact by said bonding agent into a three-dimensional porous element defining a tortuous path for passage of a gas therethrough.

27. The method of claim 26 wherein said bonding agent includes fibers comprising a thermoplastic polymer having a lower melting point than the melting point of the hydrophilic nylon polymer.

28. The method of claim 27 wherein said thermoplastic polymer of said bonding agent fibers is a polyester.

29. The method of claim 23 wherein the hydrophilic nylon fibers are bicomponent fibers comprising a sheath of said hydrophilic nylon polymer and a core of a different polymer.

30. The method of claim 29 wherein the core-forming polymer comprises polypropylene.

31. The method of claim 29 wherein said fibrous media further comprises a bonding agent, said bicomponent fibers being bonded at their points of contact by said bonding agent into a three-dimensional porous element defining a tortuous path for passage of a gas therethrough.

32. The method of claim 31 wherein said bonding agent includes fibers comprising a thermoplastic polymer having a lower melting point than the melting point of the hydrophilic nylon polymer.

33. The method of claim 32 wherein said thermoplastic polymer of said bonding agent fibers is a polyester.

34. The method of claim 33 wherein said polyester is polyethylene terephthalate.

35. The method of claim 32 wherein said bonding agent fibers are bicomponent fibers comprising a sheath of said thermoplastic polymer and a core of the same polymer as the core of the hydrophilic nylon bicomponent fibers.

36. The method of claim 21 wherein the airway is defined by an endotracheal tube communicating the patient's respiratory tract with ambient air.

37. The method of claim 21 wherein the airway connects the patient's respiratory tract with a mechanical ventilator.

38. The method of claim 21 wherein the airway connects the patient's respiratory tract with a source of oxygen.

39. The method of claim 21 wherein the airway connects the patient's respiratory tract with a source of an anesthetic.

* * * * *